US012600791B2

(12) United States Patent
Zhang et al.

(10) Patent No.: US 12,600,791 B2
(45) Date of Patent: *Apr. 14, 2026

(54) BISPECIFIC ANTIBODY, PREPARATION METHOD THEREFOR AND APPLICATION THEREOF

(71) Applicant: EXCELMAB INC., Guangzhou (CN)

(72) Inventors: Wenjun Zhang, Guangzhou (CN); Feng Li, Guangzhou (CN); Yanan Hua, Guangzhou (CN); Jiaxi Liu, Guangzhou (CN); Chunhua Fang, Guangzhou (CN)

(73) Assignee: EXCELMAB INC., Guangzhou (CN)

( * ) Notice: Subject to any disclaimer, the term of this patent is extended or adjusted under 35 U.S.C. 154(b) by 1069 days.

This patent is subject to a terminal disclaimer.

(21) Appl. No.: 17/616,043

(22) PCT Filed: Dec. 17, 2019

(86) PCT No.: PCT/CN2019/126066
§ 371 (c)(1),
(2) Date: Dec. 2, 2021

(87) PCT Pub. No.: WO2021/000530
PCT Pub. Date: Jan. 7, 2021

(65) Prior Publication Data
US 2022/0324993 A1 Oct. 13, 2022

(30) Foreign Application Priority Data
Jul. 2, 2019 (CN) .......................... 201910591110.2

(51) Int. Cl.
*C07K 16/28* (2006.01)
*A61K 39/00* (2006.01)

(52) U.S. Cl.
CPC ...... *C07K 16/2887* (2013.01); *C07K 16/2809* (2013.01); *A61K 2039/505* (2013.01); *C07K 2317/31* (2013.01); *C07K 2317/33* (2013.01); *C07K 2317/522* (2013.01); *C07K 2317/565* (2013.01); *C07K 2317/732* (2013.01); *C07K 2317/92* (2013.01); *C07K 2317/94* (2013.01); *C07K 2319/30* (2013.01)

(58) Field of Classification Search
None
See application file for complete search history.

(56) References Cited

U.S. PATENT DOCUMENTS

| 2014/0093454 A1 | 4/2014 | Teeling et al. |
| 2017/0355767 A1* | 12/2017 | Engelberts ....... A61K 39/39558 |
| 2021/0122823 A1* | 4/2021 | Zhang ..................... A61P 35/00 |

FOREIGN PATENT DOCUMENTS

| CN | 101544694 A | 9/2009 | |
| CN | 104829728 A | 8/2015 | |
| CN | 107660214 A | 2/2018 | |
| CN | 108059680 A | 5/2018 | |
| JP | 2018508188 A | 3/2018 | |
| WO | 2015063339 A1 | 5/2015 | |
| WO | 2016110576 A1 | 7/2016 | |
| WO | WO-2017205014 A1 * | 11/2017 | ........... A61K 9/0019 |
| WO | WO-2019184549 A1 * | 10/2019 | ............. A61K 47/68 |

OTHER PUBLICATIONS

Lin. Pharmacogen Per Med. 2010. 3:51-59 (Year: 2010).*
Chen et al. Adv Drug Deliv Rev. Oct. 15, 2013. 65(10):1357-1369. (Year: 2013).*
International Search Report and Written Opinion from Chinese PCT Application No. PCT/CN2019/126066 dated Mar. 16, 2020 (English Translation).
First Chinese Office Action from Chinese Application No. 201910591110.2 dated Mar. 27, 2020 (English Translation).
Second Chinese Office Action from Chinese Application No. 201910591110.2 dated Sep. 28, 2020 (English Translation).
European Office Action issued in corresponding EP Application No. 19936159.3, dated Feb. 8, 2023, 2 pages.
Japanese Office Action (with English translation) issued in corresponding JP Application No. 2021-561747, dated Oct. 17, 2022, 6 pages.

* cited by examiner

*Primary Examiner* — Anne M. Gussow
*Assistant Examiner* — Brianna K Swartwout

(57) ABSTRACT

Provided are a bispecific antibody and a preparation method therefor. The antibody comprises structural domains capable of binding to CD20 and CD3, and a heterodimer Fc region. The structural domains capable of binding to CD20 and CD3 are each independently selected from a Fab region, a ScFv region, or an sDab region. The bispecific antibody targets CD20 and CD3, and mediates T cell-specific killing of tumor cells.

12 Claims, 8 Drawing Sheets

Specification includes a Sequence Listing.

A.

B.

A.

B.

A.

B.

BISPECIFIC ANTIBODY, PREPARATION METHOD THEREFOR AND APPLICATION THEREOF

CROSS-REFERENCE TO RELATED APPLICATIONS

This application is a U.S. National Stage application under 35 U.S.C. 371 of PCT/CN2019/126066, having an international filing date of Dec. 17, 2019, which designated the United States, which PCT application claims the benefit of Chinese Patent Application No. 201910591110.2, filed on Jul. 2, 2019, of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Nov. 30, 2021, is entitled "046231_000052_sequence_listing" and is 30 kb in size.

TECHNICAL FIELD

The present disclosure relates to an antibody, a preparation method therefor, and use thereof, and in particular to a bispecific antibody, a preparation method therefor, and use thereof.

BACKGROUND ART

Specific antigens such as CD19, CD20, CD22, and CD52 on the surface of B cells are potential targets for treatment of B cell-related diseases. Among them, CD20 protein is also called B lymphocyte restricted differentiation antigen, Bp35, or B1, which is a tetra-transmembrane, highly hydrophobic, non-glycosylated phosphoprotein encoded and expressed by the human MS4A1 gene, with a molecular weight of about 35kD. CD20 is specifically expressed on the surfaces of pre-B cells and mature B cells, but not expressed in hematopoietic stem cells, progenitor cells, plasma cells and other normal somatic cells. CD20 is also expressed on the surface of cells of B-cell lymphomas such as non-Hodgkin's lymphoma (NHL) and chronic lymphocytic leukemia (CLL). There is no known natural ligand for CD20. Studies have shown that CD20 has calcium ion channel activity. It regulates the cell cycle by regulating the concentration of calcium ions in cells, plays a special role in the activation of B cells, i.e., in the process of the differentiation and growth of B cells from the G0 phase to the G1 phase, and regulates the cell cycle from the S phase to the mitosis phase, and can also induce cell apoptosis.

CD20 is specifically expressed on the surfaces of cells of a variety of B cell-related lymphomas, no CD20 is expressed on pre-B cells and other somatic cells, and CD20 is not easily shed or secreted and is not endocytosed after binding to antibodies, therefore CD20 is an ideal target with great potential for the treatment of B cell-related diseases. Currently, a variety of therapeutic monoclonal antibody drugs for CD20 have been commercially available. They can be divided, according to the mechanism of action, into two types: Type I and Type II. Antibodies of Type I mainly function through complement-dependent cytotoxicity (CDC) and antibody-dependent cytotoxicity (ADCC). Type II mainly functions through programmed cell death (PCD) and ADCC. Rituximab (trade name: Rituxan/Mabthera), which is a human-mouse chimeric antibody, is a first-generation CD20 antibody (Type 1), which has been approved by the FDA in 1997 for the treatment of NHL and subsequently approved for the treatment of diseases including rheumatoid arthritis and CLL. Ofatumumab (trade name: Arzerra), which is a fully humanized monoclonal antibody, is a second-generation CD20 antibody (Type I). Ofatumumab has stronger affinity to CD20 than that of Rituximab (trade name: Rituxan) and elicits a stronger CDC response and a similar ADCC response with Rituximab, as shown by cell tests. It has gained accelerated approval from the FDA in 2009 for the treatment of CLL ineffectively treated with fludarabine or alemtuzumab, and is later approved for the treatment of diseases including follicular lymphoma, optic neuromyelitis, and diffuse and relapsing multiple sclerosis. Obinutuzumab (trade name: Gazyva), which is a humanized monoclonal antibody, is a third-generation CD20 antibody (Type II), which elicits a stronger ADCC response than Rituximab, due to increased affinity of the antibody to NK cells, macrophages, and dendritic cells resulting from the glycosylation modification. Moreover, Obinutuzumab can more effectively induce apoptosis of B cells through neutrophil-induced endocytosis and cell death and is approved by the FDA in 2013 for use in combination with chlorambucil to treat CLL that has not been treated in the past.

Compared with traditional chemotherapy, monoclonal antibody drugs targeting CD20 target have shown better clinical advantages, but they often need to be used in combination with chemical drugs, and not all patients can respond to the CD20 antibody therapy. This is because the therapeutic effects of CD20 monoclonal antibodies are related to the levels of expression of CD20 on tumor cells. CD20 is expressed on certain types of cells such as CLL cells at a significantly lower level than on other types of B-cell tumors, which limits the therapeutic effects of CD20 monoclonal antibodies. In addition, monoclonal antibodies kill tumor cells mainly by ADCC, ADCP, CDC and other mechanisms of action produced by binding to FcγR. However, FcγR is polymorphic among individuals, resulting in significant differences in the affinity of FcγR to Fc, thereby reducing the overall efficacy of the drugs and leading to relapse and development of drug resistance. Once a patient relapses, he/she will be treated with greater difficulty, will have an extremely poor prognosis, and may have a median survival time of only 2 to 8 months. T cells with a high tumor-killing effect cannot be effectively activated in the absence of FcγR. Therefore, it is necessary to design more effective clinical antibody drugs to meet the current therapeutic needs, for example, to activate T cells to kill tumor cells more efficiently, or develop multi-specific antibodies that simultaneously bind to two or more antigen targets.

Because bispecific antibodies can simultaneously bind to epitopes of two antigens or to two epitopes of one antigen, higher potency can be achieved through synergistic effect. Some bispecific antibodies can recruit effector cells (such as T cells) to target sites and directly kill the target cells by activating T cells. At present, the safety and efficacy of bispecific antibodies have been greatly improved, and they have been widely used in the treatment of tumors and autoimmune diseases, have become a hot topic of research and development in tumor immunotherapy, and have a broad prospect of application. In the practical use in the treatment of malignant tumors, bispecific antibodies usually simultaneously bind to antigens on the surface of tumor cells and to antigens on the surface of immune cells and kill the tumor cells by activating the autoimmune system.

CD3 is a homodimeric or heterodimeric protein complex, which is an important component constituting a T-cell receptor (TCR). Its intracellular region contains an immunoreceptor tyrosine-based activation motif (ITAM). When the ITAM is phosphorylated, it will bind to the kinase ZAP70, thereby transducing T cell activation signals downstream. Antibodies that target CD3 can accumulate CD3 on the surface of T cells, thereby activating the T cells. This process mimics the process of TCR recognition of MHC-antigen peptides. Bispecific antibodies with resistance to CD3 and resistance to tumor-specific antigens can simultaneously bind to T cells and tumor cells, activate and guide T cells to secrete granzymes, perforin and the like to kill tumor cells. For example, bispecific antibodies that simultaneously bind to CD20 and CD3 molecules can recruit T cells to tumor cells expressing CD20 protein, causing CD20-positive tumor cells to be killed and eliminated.

In early days, bispecific antibodies were mostly produced by chemical cross-linking of purified monoclonal antibodies or by the fusion of hybridoma cells expressing two different monoclonal antibodies. However, products produced by these methods have many problems. For example, the products are unstable and have low yields, and the antibodies are modified improperly, have immunogenicity, and are produced and purified with difficulty. With the advancement of genetic engineering technologies in recent years, a lot of BsAbs have been prepared by genetic engineering technologies. There are currently more than 60 different bispecific antibody forms, which can be generally divided into two categories: bispecific antibodies containing no Fc and bispecific antibodies containing Fc regions. The bispecific antibodies containing no Fc, such as BiTE, DART, TandAbs, Bi-Nanobody, etc., have small molecular weights, can be expressed in prokaryotic cells, are produced with reduced complexity, and can easily penetrate into tissues and tumor cells to reach targets, but they cannot mediate Fc-related biological functions, will be quickly eliminated in vivo, and have a short half-life. If a non-natural peptide chain linking fragment or additional structure is introduced into an antibody, the relative molecular weight and physical and chemical properties of the antibody will be quite different from those of a natural IgG antibody, and it is easier to form multimers and produce immunogenicity. The bispecific antibodies containing Fc can mediate ADCC and CDC to increase the (FcRn-mediated) half-life, stability, and solubility of the antibodies in the blood, and also include regions binding to protein A and protein G, to facilitate the purification of downstream products. This type of bispecific antibody technologies includes TrioMab, Knob-into-hole, DVD-Ig, DuoBody, SEEDbody, BEAT, etc.

SUMMARY

The objective of the present disclosure includes, for example, providing a stable and efficient CD20- and CD3-targeting bispecific antibody which can mediate specific killing of tumor cells by T cells, in order to overcome the above-mentioned shortcomings of the prior art.

In the first aspect, the present disclosure provides a bispecific antibody comprising a domain capable of binding to CD20, a domain capable of binding to CD3, and a heterodimeric Fc region, wherein the domain capable of binding to CD20 and the domain capable of binding to CD3 are each independently selected from a Fab region, a ScFv region, or a sDab region.

The most ideal bispecific antibody is a bispecific antibody maintaining the natural structure of an IgG antibody, which involves addressing the problem of mispairing between heavy and light chains during assembly of the antibody. In the present disclosure, a bispecific antibody that simultaneously targets leukocyte differentiation antigen 20 (CD20) and leukocyte differentiation antigen 3 (CD3) is prepared by using an artificial modified pairing method, in which a small number of amino acids of Fc and at the heavy chain-light chain interface of the antibody are changed and very few site mutations are introduced without affecting the structure and function of the antibody. Compared with traditional monoclonal antibodies, the CD20×CD3 bispecific antibody has the advantages of: (1) activating $CD4^+$ and $CD8^+$ T cells to specifically kill tumor cells positive for expression of CD20, including tumor cells on which CD20 is expressed at low levels; (2) having an efficient tumor killing effect even at a very low dose used; (3) being capable of inducing low-level cytokine release with higher safety; and (4) having a structure similar to that of a natural IgG antibody and having similar stability, half-life, and physical and chemical properties to those of monoclonal antibodies. The bispecific antibody can be used in multiple application fields such as in the treatment and diagnosis of diseases.

The bispecific antibody of the present disclosure can specifically bind to CD20 epitope and CD3 epitope, and mediate antigen-specific activation of T cells. It is a novel, stable, and efficient CD20- and CD3-targeting bispecific antibody (i.e., CD20×CD3 BsAb) that can mediate specific killing of tumor cells by T cells, and it can cross-react with CD20 and CD3 of a human being and a primate animal.

The bispecific antibody of the present disclosure consists of three or four polypeptide chains, wherein the three-chain structure includes a heavy chain, a light chain, and a scFv-Fc chain, and the four-chain structure includes two heavy chains and two light chains. The bispecific antibody forms an immunoglobulin domain that specifically binds to CD20, an immunoglobulin domain that specifically binds to CD3, and a heterodimeric Fc region. The two heavy chains (or the one heavy chain and the scFv-Fc chain) interact with and bind to each other to form a heterodimer form, thereby forming the above-mentioned heterodimeric Fc region. In the four-chain bispecific antibody, the two light chains each bind to one of the heavy chains to form the Fab structure that specifically binds to CD20 and the Fab structure that specifically binds to CD3 as mentioned above. It should be particularly noted that the CD20×CD3 BsAb according to the present disclosure contains an Fc region, which can increase the half-life and stability of the antibody in a body.

In one or more embodiments of the bispecific antibody of the present disclosure, the domain capable of binding to CD20 comprises the first immunoglobulin Fab region which is formed by the first heavy chain and the first light chain binding to each other. A variable region of the first heavy chain has an amino acid sequence as set forth in SEQ ID No: 2, and a variable region of the first light chain has an amino acid sequence as set forth in SEQ ID No: 4; and/or the domain capable of binding to CD3 comprises the second immunoglobulin Fab region which is formed by the second heavy chain and the second light chain binding to each other. A variable region of the second heavy chain has an amino acid sequence as set forth in SEQ ID No: 6, and a variable region of the second light chain has an amino acid sequence as set forth in SEQ ID No: 10; and the heterodimeric Fc region is composed of two polypeptide chains, each of which contains oppositely charged asymmetric amino acid modifications.

In one or more embodiments of the bispecific antibody of the present disclosure, a CH1 portion of the first heavy chain and a CL portion of the first light chain both contain one non-cysteine residue substituted for a native cysteine residue and one cysteine residue substituted for a non-cysteine.

In one or more embodiments of the bispecific antibody of the present disclosure, a disulfide bond is formed by the cysteine residue substituted for a non-cysteine in the CH1 portion of the first heavy chain and the cysteine residue substituted for a non-cysteine in the CL portion of the first light chain.

In one or more embodiments of the bispecific antibody of the present disclosure, in the CH1 portion of the first heavy chain, the non-cysteine residue substituted for a native cysteine residue is C220S, and the cysteine residue substituted for a non-cysteine is L128C.

In one or more embodiments of the bispecific antibody of the present disclosure, in the CL portion of the first light chain, the non-cysteine residue substituted for a native cysteine residue is C214S, and the cysteine residue substituted for a non-cysteine is F118C.

In one or more embodiments of the bispecific antibody of the present disclosure, the second immunoglobulin Fab region does not contain a non-cysteine residue substituted for a native cysteine residue and does not contain a cysteine residue substituted for a non-cysteine residue.

In one or more embodiments of the bispecific antibody of the present disclosure, the domain capable of binding to CD20 comprises the first immunoglobulin Fab region, and the domain capable of binding to CD3 comprises the second immunoglobulin Fab region; and the first heavy chain and the second heavy chain bind to each other to form a heterodimeric Fc region.

In one or more embodiments of the bispecific antibody of the present disclosure, the hinge region of the first heavy chain and the hinge region of the second heavy chain are covalently bonded by at least one disulfide bond.

In one or more embodiments of the bispecific antibody of the present disclosure, the first heavy chain and the second heavy chain both contains a CH2 domain and a modified CH3 domain, and the CH2 domain and the modified CH3 domain of the first heavy chain and the CH2 domain and the modified CH3 domain of the second heavy chain bind to each other to form a heterodimeric Fc region.

In one or more embodiments of the bispecific antibody of the present disclosure, at least one of the CH2 domains of the first heavy chain and the second heavy chain contains one, two, or more mutation sites. The mutation site(s) is used for reducing the binding of Fc to its receptor FcγR. In one or more embodiments of the bispecific antibody of the present disclosure, the mutation combination is L234A/L235A.

In one or more embodiments of the bispecific antibody of the present disclosure, the modified CH3 domain in the first heavy chain and the modified CH3 domain in the second heavy chain include oppositely charged asymmetric amino acid modifications to form a heterodimeric Fc region. The inclusion of oppositely charged asymmetric amino acid modifications can facilitate the formation of heterodimers.

In one or more embodiments of the bispecific antibody of the present disclosure, the modified CH3 domain in the first heavy chain contains at least one of P395K, P396K, and V397K mutations, and the modified CH3 domain in the second heavy chain contains at least one of T394D, P395D, and P396D mutations; or the modified CH3 domain in the first heavy chain contains at least one of T394D, P395D, and P396D mutations, and the modified CH3 domain in the second heavy chain contains at least one of the P395K, P396K, and V397K mutations.

In one or more embodiments of the bispecific antibody of the present disclosure, the first heavy chain and the second heavy chain are derived from a human antibody IgG1, IgG2, IgG3, or IgG4. In one or more embodiments of the bispecific antibody of the present disclosure, the first heavy chain and the second heavy chain are derived from a human antibody IgG1.

In one or more embodiments of the bispecific antibody of the present disclosure, the first heavy chain has an amino acid sequence as set forth in SEQ ID No: 1, the first light chain has an amino acid sequence as set forth in SEQ ID No: 3, the second heavy chain has an amino acid sequence as set forth in SEQ ID No: 5 or SEQ ID No: 7, and the second light chain has an amino acid sequence as set forth in SEQ ID No: 9.

In one or more embodiments of the bispecific antibody of the present disclosure, the domain capable of binding to CD20 comprises the first immunoglobulin Fab region, and the domain capable of binding to CD3 comprises a scFv-Fc fusion protein polypeptide chain; a scFv region in the scFv-Fc fusion protein polypeptide chain comprises a heavy chain variable region having an amino acid sequence as set forth in SEQ ID No: 6 and a light chain variable region having an amino acid sequence as set forth in SEQ ID No: 10, and the first heavy chain and the scFv-Fc fusion protein polypeptide chain bind to each other to form a heterodimeric Fc region; or the domain capable of binding to CD20 comprises a scFv-Fc fusion protein polypeptide chain, and the domain capable of binding to CD3 comprises the second immunoglobulin Fab region; the scFv-Fc fusion protein polypeptide chain has an amino acid sequence as set forth in SEQ ID No: 2 and comprises a light chain variable region having an amino acid sequence as set forth in SEQ ID No: 4, and the second heavy chain and the scFv-Fc fusion protein polypeptide chain bind to each other to form a heterodimeric Fc region.

In one or more embodiments of the bispecific antibody of the present disclosure, the domain capable of binding to CD20 comprises the first immunoglobulin Fab region, and the domain capable of binding to CD3 comprises a scFv-Fc fusion protein polypeptide chain; the variable region of the first heavy chain has an amino acid sequence as set forth in SEQ ID No: 8; and the scFv region in the scFv-Fc fusion protein polypeptide chain has an amino acid sequence as set forth in SEQ ID No: 11, a heavy chain variable region CDR3 in the scFv-Fc fusion protein polypeptide chain contains a N106T mutation, and the sequence of the mutated CDR3 is amino acids 101-113 of SEQ ID NO: 8.

In one or more embodiments of the bispecific antibody of the present disclosure, the scFv region in the scFv-Fc fusion protein polypeptide chain has an amino acid sequence as set forth in SEQ ID No: 12, SEQ ID No: 13, or SEQ ID No: 14, or its variable region has an amino acid sequence as set forth in SEQ ID No: 2, SEQ ID No: 4, SEQ ID No: 8, SEQ ID No: 6, or SEQ ID No: 10.

In the second aspect, the present disclosure provides an expression vector, which is obtained by linking a DNA sequence corresponding to the above-mentioned amino acid sequence to a basic vector.

In one or more embodiments of the bispecific antibody of the present disclosure, the expression vector is a plasmid, a viral vector, or a recombinant expression vector.

In one or more embodiments of the bispecific antibody of the present disclosure, the basic vector is pFUSE-hIgG 1-Fc2.

In the third aspect, the present disclosure provides a host cell containing the above-mentioned expression vector.

In one or more embodiments of the bispecific antibody of the present disclosure, the host cell is a mammalian cell. In one or more embodiments of the bispecific antibody of the present disclosure, the host cell is a CHO cell or a HEK293 cell.

In the fourth aspect, the present disclosure provides a method for preparing the above-mentioned bispecific antibody, which includes the steps of:

(a) constructing an expression vector, which is obtained by linking a nucleotide encoding the bispecific antibody to a basic vector;

(b) transfecting or transforming the expression vector constructed in step (a) into a host cell, and culturing the host cell; and (c) isolating and purifying the bispecific antibody.

In one or more embodiments of the bispecific antibody of the present disclosure, the isolation and purification of the bispecific antibody is carried out by protein A affinity chromatography, a cation exchange method, or an anion exchange method.

In the fifth aspect, the present disclosure provides an antibody conjugate, which is formed by conjugating a conjugating substance to the above-mentioned bispecific antibody.

In one or more embodiments of the bispecific antibody of the present disclosure, the conjugating substance is a cytotoxin, a radioisotope, a fluorescent label, a luminescent substance, a chromogenic substance, or an enzyme.

In the sixth aspect, the present disclosure provides a pharmaceutical composition, comprising the above-mentioned bispecific antibody.

In the seventh aspect, the present disclosure provides use of the above-mentioned bispecific antibody in preparation of a medicament or a pharmaceutical composition for treating tumors, rheumatoid arthritis, multiple sclerosis, or systemic lupus erythematosus.

In one or more embodiments of the bispecific antibody of the present disclosure, the tumors are malignant tumors associated with expression of CD20.

In one or more embodiments of the bispecific antibody of the present disclosure, the malignant tumors are acute B lymphocytic leukemia (B-ALL), diffuse large B-cell lymphoma (DLBCL), chronic lymphocyte Leukemia (CLL), follicular lymphoma, non-Hodgkin's lymphoma (NHL), chronic myelogenous leukemia (CML), or Burkitt's lymphoma.

In the eighth aspect, the present disclosure provides use of the above-mentioned bispecific antibody in a medicament or a pharmaceutical composition.

In the ninth aspect, the present disclosure provides use of the above-mentioned bispecific antibody in the treatment of tumors, rheumatoid arthritis, multiple sclerosis, or systemic lupus erythematosus.

Compared with the prior art, the present disclosure has the following advantageous effects.

(1) The CD20×CD3 BsAb molecule according to the present disclosure maintains the structure of a natural IgG antibody or approximates to the structure of a natural IgG antibody and has similar stability and physical and chemical properties to those of monoclonal antibodies.

(2) The present disclosure relates to the construction of a bispecific antibody. A small number of amino acids in the heavy chain and light chain are mutated so that the two polypeptide chains have opposite charges to facilitate the formation of a heavy-chain heterodimer, and a non-natural disulfide bond is introduced to overcome mispairing of light chains. This method involves very few mutations, has very little effect on the function of the Fc region and does not affect the expression yield of proteins in eukaryotic cells.

(3) Compared with monoclonal antibodies, the CD20× CD3 BsAb molecules according to the present disclosure can simultaneously bind to antigens on the surface of tumor cells and to CD3 molecules on the surface of T cells and increase the targeted tumor killing effect of T cells by means of antigen-specific activation of TCR, therefore a significant tumor cell killing effect can be achieved with a smaller amount of the antibody.

(4) Compared with small molecular bispecific antibodies such as BiTE, the CD20×CD3 BsAb molecule according to the present disclosure contains an antibody Fc region, so that the half-life and stability of the antibody are increased, and it is easier to use the existing monoclonal antibody purification technology to simplify the process of production of bispecific antibodies.

(5) Compared with CD20-targeting chimeric antigen receptor T-cell immunotherapy (CAR-T), the present disclosure does not involve exogenous viruses and operations such as in-vitro culture and reinfusion of T cells, and thus has fewer toxic and side effects and is safer and more controllable.

(6) The present disclosure involves a modification for weakening affinity to CD3 to improve the safety of bispecific antibody molecules for CD3.

BRIEF DESCRIPTION OF THE DRAWINGS

FIG. 2 shows CD20×CD3 BsAbs purified by protein A affinity chromatography, wherein FIG. 2A shows diagrams of non-reducing and reducing SDS-PAGE gel electrophoresis of CD20×CD3 BsAb V1 purified with protein A in one step, FIG. 2B shows diagrams of non-reducing and reducing SDS-PAGE gel electrophoresis of CD20×CD3 BsAb V2 purified with protein A in one step, and FIG. 2C shows diagrams of non-reducing and reducing SDS-PAGE gel electrophoresis of a CD20×CD3 BsAb (a three-chain bispecific antibody comprising an anti-CD20 scFv domain and an anti-CD3 Fab domain) purified with protein A in one step;

FIG. 5 is a graph showing the results of detection of the binding ability of CD20×CD3 bispecific antibodies to antigen CD3, wherein FIG. 5A shows the affinities of CD20× CD3 BsAbs V1 and V2 to CD3 antigen molecules as compared by ELISA, where the CD20×CD3 BsAb V1 binds to the CD3 antigen at an EC50 concentration of 0.8178 µg/mL, and the CD20×CD3 BsAb V2 binds to the CD3 antigen at an EC50 concentration of 2.097 µg/ml; and FIG. 5B shows the binding ability of three-chain bispecific antibodies to CD3 antigen molecules, where curve 1 represents a four-chain bispecific antibody comprising a Fab domain binding to CD20 and a Fab domain binding to CD3, which binds to the CD3 antigen at an EC50 concentration of 4.9 µg/ml; curve 2 represents a three-chain bispecific antibody comprising a scFv domain binding to CD20 and a Fab domain binding to CD3, which binds to the CD3 antigen at an EC50 concentration of 4.9 µg/ml; and curve 3 represents a three-chain bispecific antibody comprising a Fab domain binding to CD20 and a scFv domain binding to CD3, which binds to the CD3 antigen at an EC50 concentration of 0.6 µg/ml;

FIG. 7C shows the detected activity to kill target cells (Daudi cells) mediated by CD20×CD3 three-chain bispecific antibodies, where curve 1 represents a three-chain bispecific antibody comprising a scFv domain binding to CD20 and a Fab domain binding to CD3; curve 2 represents a three-chain bispecific antibody comprising a Fab domain binding to CD20 and a scFv domain binding to CD3; and curve 3 represents a four-chain bispecific antibody comprising a Fab domain binding to CD20 and a Fab domain binding to CD3;

DETAILED DESCRIPTION OF THE EMBODIMENTS

Figure 1:
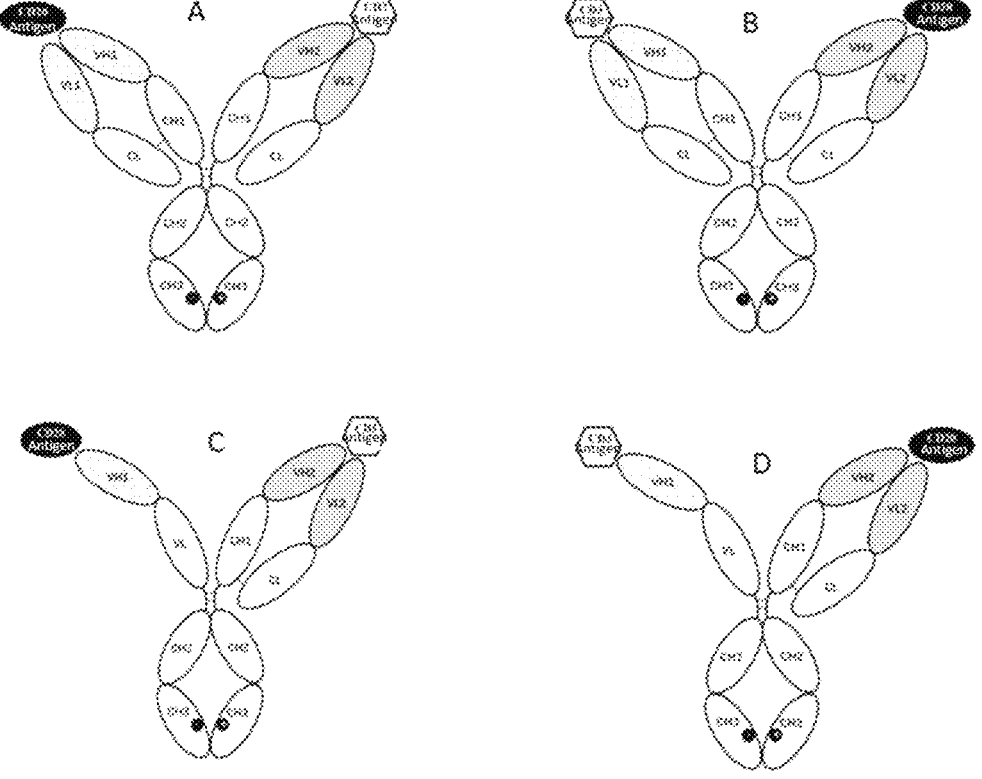
FIG. 1 is a schematic diagram showing examples of the structure of a CD20×CD3 BsAb according to the present disclosure.

The present disclosure will be further described below with reference to the accompanying drawings and specific embodiments in order to better illustrate the objectives, technical solutions, and advantages of the present disclosure. Also, in order to provide a better understanding of the present disclosure, definitions and explanations of related terms are provided below.

BsAb: bispecific antibody
HC: heavy chain
LC: light chain
VH: variable region of heavy chain
VL: variable region of light chain
CH: constant region of heavy chain
CL: constant region of light chain
CDR: complementarity determining region
scFv: single-chain variable fragment
ADCC: antibody dependent cellular cytotoxicity
ELISA: enzyme-linked immunosorbent assay
FACS: fluorescence-activated cell sorting, i.e., flow cytometry
EC50: half maximal effective concentration Related terms used in the present disclosure have the same meanings as commonly understood in the technical field, unless otherwise defined. The operating steps of tests such as molecular cloning, cell culture, protein purification, immunological experiments, microbiology, and animal models described in the present disclosure are routine steps widely used in the art. Singular terms in the present disclosure include pluralities and plural meanings include singular meanings, unless otherwise stated in context. Nucleotide sequences described in the present disclosure are arranged and written from left to right in the direction from the 5' end to the 3' end, unless otherwise specified. Amino acid sequences described in the present disclosure are arranged and written from left to right in the direction from the amino terminus (N terminus) to the carboxy terminus (C terminus), unless otherwise specified. The three-letter abbreviations for amino acids and the one-letter abbreviations for nucleotides mentioned in the present disclosure are in the forms generally accepted in the technical field, and the one-letter abbreviations for amino acids are in the forms recommended by the IUPAC-IUB Biochemical Nomenclature Commission.

The term "amino acid" refers to one of the 20 naturally occurring amino acids or any non-natural analogs that may be present at a specific defined position. The term "amino acid mutation" described in the present disclosure refers to an amino acid substitution, insertion, deletion, or modification in a polypeptide sequence, and any combination of an amino acid substitution, insertion, deletion, and modification. The preferred amino acid modification herein is a substitution. In the present disclosure, "amino acid substitution" or "substitution" refers to replacement of an amino acid at a particular position in a parent polypeptide sequence with another amino acid. For example, the substitution C220S refers to a variant polypeptide, in which amino acid Cysteine at position 220 of the polypeptide has been replaced with amino acid Serine. Amino acid mutations can be achieved by molecular cloning or chemical methods. The molecular cloning methods include PCR, site-directed mutagenesis, full gene synthesis, etc.

The terms "protein", "peptide chain", and "polypeptide chain" refer to molecules in which two or more amino acids are linked by peptide bonds, including natural proteins, artificial proteins, protein fragments, mutant proteins, fusion proteins, and the like.

The term "domain" refers to a specific structural region with independent functions in a biological macromolecule. A domain has an independent tertiary structure and its function does not depend on the remaining moiety of the biological macromolecule. The domain in the present disclosure refers particularly to a region in a protein, such as a domain of a heavy chain variable region VH or a domain of a light chain variable region VL. Domains may bind to each other to form a large domain.

The term "CD3" refers to the cluster of differentiation-3 protein, which is a component constituting a T cell receptor complex (TCR) expressed on the surface of T cells. It is a homodimer or heterodimer consisting of four peptide chains including CD3δ (human CD3δ, UniProt Entry No. P0423), CD3ε (human CD3ε, UniProt Entry No. P07766), CD3γ (human CD3γ, UniProt Entry No. P09693) and CD3ζ ((human CD3ζ, UniProt Entry No. P20963). The "CD3" mentioned in the present disclosure is human CD3, unless explicitly specified as, for example, "cynomolgus monkey CD3" or "mouse CD3".

The "polypeptide chain that binds to CD3" or "antibody that binds to CD3" as described in the present disclosure includes an antibody or antibody fragment that specifically binds to a CD3 single chain unit, and an antibody or antibody fragment that specifically binds to a CD3 homodimer or heterodimer. The antibodies that specifically bind to CD3 as described in the present disclosure can bind both to CD3 protein molecules and to CD3 expressed on the surface of cells.

The term "CD20" refers to the B lymphocyte restricted differentiation antigen (human CD20, UniProt Entry No. P11836) encoded and expressed by the human MS4A1 gene, including variants and subtypes of the human CD20 proteins expressed naturally by cells and expressed by cells transfected with foreign genes, and homologous proteins of other species (e.g., cynomolgus monkey CD20 protein).

The term "antibody" refers to an immunoglobulin molecule containing at least one antigen-recognition site and capable of specifically binding to an antigen. Here, the term "antigen" refers to a substance that can induce an immune response in a body and specifically binds to an antibody, such as a protein, polypeptide, peptide, carbohydrate, polynucleotide, lipid, or hapten, or a combination thereof. The binding of an antibody to an antigen is mediated by an interaction created therebetween, including a hydrogen bond, a van der Waals force, an ionic bond, and a hydrophobic bond. A region on the surface of an antigen that binds to an antibody is called an "antigenic determinant" or "epitope". Generally, each antigen has multiple determinants. The term "antibody" mentioned in the present disclosure includes monoclonal antibodies (including full-length monoclonal antibodies), polyclonal antibodies, antibody fragments, multi-specific antibodies (e.g., bispecific antibodies) containing at least two different epitope binding domains, human antibodies, humanized antibodies, post-translationally modified antibodies, camelid antibodies, chimeric antibodies, fusion proteins containing antibody antigenic determinants, and any other modified immunoglobulin molecules containing antigen recognition sites, as long as these antibodies exhibit the desired biological activity. Specifically, antibodies include immunoglobulin molecules and immunologically active fragments of immunoglobulin molecules, namely molecules containing at least one antigen binding site.

Light chains of a natural human antibody are covalently linked to heavy chains via two disulfide bonds, and the heavy chain-light chain dimers then form an antibody molecule similar to the letter Y by means of disulfide bonds formed between the heavy chains. There are different numbers of disulfide bonds among the heavy chains of different types of human antibodies. A region between the two arms and the trunk of the Y shape is a hinge region, which has a certain degree of flexibility. Each antibody polypeptide chain includes a variable region and a constant region, which are spatially folded to form different domain units. Each light chain is composed of a variable region domain VL at the amino terminus and a constant region domain CL at the carboxy terminus. Each heavy chain is composed of a variable region domain VH at the amino terminus and the following three or four constant region domains (CH1, CH2, CH3, and CH4).

The variable region of an antibody is an antigen-binding region, including a heavy chain variable region (VH) and a light chain variable region (VL). VH and VL have similar structures. The variable regions of the heavy chain and light chain are composed of three complementarity determining regions (CDR) and four framework regions (FR) flanking the CDRs, respectively. The framework regions support the CDRs and define the spatial relationships between the respective CDRs. The CDRs of the variable region are hypervariable in sequence, and thus are also called hypervariable regions (HVR). CDRs form a specific loop structure and directly participate in antigen recognition. Each variable region domain contains three HVRs. The HVRs in VH are H1, H2, and H3, respectively, and the HVRs in VL are L1, L2, and L3, respectively. The CDRs of the heavy chain or the light chain are represented as CDR1, CDR2, and CDR3 from the amino terminus, respectively. The variable regions of the heavy chain and the light chain are bound by non-covalent bonds. An antigen recognition site is formed by the three CDRs of the heavy chain together with the three CDRs of the light chain. This part of amino acid residues is the main body of the antibody participating in antigen binding and gives the antibody its specificity for recognizing an antigen.

The term "Fab", "Fab region", "Fab fragment", or "Fab molecule" refers to an antigen-binding fragment, containing a VH domain and CH1 domain of a heavy chain and a VL domain and CL domain of a light chain of an immunoglobulin, where the first constant region domain CH1 of the heavy chain is bound to the constant region domain CL of the light chain, and the variable region domain VH of the heavy chain is bound to the variable region domain VL of the light chain.

The term "Fc", "Fc region", "Fc fragment", or "Fc molecule" refers to an effector region of an antibody, which can induce, for example, CDC, ADCC, ADCP, and cytokine release. The Fc of a natural antibody is usually formed by binding two identical protein fragments, each containing two or three immunoglobulin constant region domains. The Fc described in the present disclosure includes natural Fc and mutated Fc. Although the boundaries of the Fc region may vary, the Fc region of a human IgG heavy chain is usually defined to include residues from C226 or P230 to its carboxy terminus. Under the experimental conditions, fragments Fab and Fc are generated by papain digestion for an immunoglobulin monomer, respectively. The "hinge" or "hinge region" of an antibody refers to a flexible polypeptide comprising amino acids between the first and second constant domains (CH1 and CH2) of the antibody.

The Fc contained in the bispecific antibody described in the present disclosure is a human immunoglobulin Fc. Under normal circumstances, the human immunoglobulin Fc region has a polypeptide sequence derived from a wild-type human immunoglobulin Fc region. The wild-type human immunoglobulin Fc refers to an amino acid sequence commonly present in the human population, which also contains polymorphisms in different positions of the Fc region among certain individuals. The human immunoglobulin Fc described in the present disclosure also includes changes of several amino acids of the wild-type human immunoglobulin Fc, for example, change of some interface amino acids in the Fc region for formation of a heavy-chain heterodimer.

Amino acids of a variable region of an antibody described in the present disclosure are numbered by using the numbering scheme set forth by Kabat et al. in 1991, namely, the "Kabat index" or "Kabat numbering", unless otherwise specified. Amino acids of a constant region of an antibody described in the present disclosure are numbered by using the EU index, unless otherwise specified.

The term "antigen-binding site" refers to one or more amino acid residues of an antigen-binding molecule that directly interact with an antigen. The antigen-binding site of an antibody is composed of an antigen complementary determining region (CDR). A natural immunoglobulin molecule usually contains two antigen-binding sites. A Fab molecule usually contains one antigen-binding site.

The term "T cell activation (or activation of T cells)" refers to one or more immune responses of T lymphocytes, especially killer T lymphocytes, including: proliferation, differentiation, release of cytokines, secretion of killer effector molecules, cell killing, etc.

The term "EC50", i.e., a half maximal effective concentration, refers to the corresponding concentration of an antibody that induces 50% of the maximum effect.

As used herein, "specific binding (or specifically bind)" refers to a non-random binding reaction between two molecules, such as a reaction between an antibody and its targeted antigen. In certain embodiments, an antibody that specifically binds to a certain antigen (or an antibody specific to a certain antigen) refers to an antibody binding to the antigen with an affinity ($K_D$) less than about $10^{-5}$ M, for example, less than about $10^{-6}$ M, $10^{-7}$ M, $10^{-8}$ M, $10^{-9}$ M, or $10^{-10}$ M or less. In some embodiments of the present disclosure, the term "targeting" refers to specific binding.

As used herein, "$K_D$" refers to a dissociation equilibrium constant for a specific antibody-antigen interaction and is used for describing the binding affinity between an antibody and an antigen. A smaller equilibrium dissociation constant indicates a tighter binding between an antibody and an antigen and a higher affinity between the antibody and the antigen. Generally, an antibody binds to an antigen with an equilibrium dissociation constant ($K_D$) less than about $10^{-5}$ M, for example, less than about $10^{-6}$ M, $10^{-7}$ M, $10^{-8}$ M, $10^{-9}$ M, or $10^{-10}$ M or less.

The term "single-chain variable fragment" or "scFv" refers to a fusion protein comprising a heavy chain variable region VH and a light chain variable region VL of an immunoglobulin, including different combination forms of VH at the N-terminus and VL at the N-terminus, which can be prepared by using a conventional molecular cloning method for constructing recombinant proteins (Sambrook J F, E. F. et al., Molecular cloning: a laboratory manual. 4th ed., Cold Spring Harbor Laboratory Press, Cold Spring Harbor, New York: 2012).

The term "humanized antibody" refers to an antibody or antibody fragment obtained by replacing some or all of CDR regions of a humanized immunoglobulin (receptor antibody) with CDR regions of a non-humanized antibody (donor antibody), wherein the donor antibody may be a non-humanized (e.g., mouse, rat, or rabbit) antibody with the expected specificity, affinity, or reactivity. Furthermore, some amino acid residues in the framework region (FR) of the acceptor antibody may also be replaced with corresponding amino acid residues of the non-humanized antibody, or with amino acid residues of other antibodies, to further improve or optimize one or more characteristics of the antibody.

The term "bispecific antibody" refers to an antibody molecule capable of binding to two independent antigens or having binding specificity to different epitopes in the same antigen. For example, in some embodiments, a bispecific antibody molecule has one arm binding to a tumor-associated antigen, and the other arm binding to an immune cell-associated antigen (e.g., a CD3 molecule), so that cellular immune-related mechanisms can be activated and initiated at tumor cells.

Bispecific antibodies may also be conjugated with cytotoxins (e.g., radioisotopes, vinca alkaloids, methotrexate, etc.), radioisotopes, fluorescent labels, luminescent substances, chromogenic substances, or enzymes. In some embodiments, a moiety conjugated to an antibody or bispecific antibody of the present disclosure for forming an antibody conjugate is a cytotoxin. In some embodiments, the cytotoxin refers to a substance that inhibits or prevents cell functions and/or causes cell destruction, and includes small molecule cytotoxins. In some embodiments, the cytotoxin is selected from colchicine, emtansine, maytansinoid, auristatin, vindesine, tubulysin, and the like. In some embodiments, the moiety conjugated to an antibody or bispecific antibody of the present disclosure for forming an antibody conjugate is a radioisotope. In some embodiments, the radioisotope includes radioisotopes such as $At^{211}$, $I^{131}$, $I^{125}$, $Y^{90}$, $Re^{186}$, $Re^{188}$, $Sm^{153}$, $Bi^{212}$, $P^{32}$, and Lu. In some embodiments, the moiety conjugated to an antibody or bispecific antibody of the present disclosure for forming an antibody conjugate is selected from a fluorescent label, a luminescent substance, and a chromogenic substance, such as fluorescein isothiocyanate (FITC), luciferase, horseradish peroxidase (HRP), and the like. In some embodiments, the moiety conjugated to an antibody or bispecific antibody of the present disclosure for forming an antibody conjugate is an enzyme, such as an enzyme-active toxin derived from bacteria, fungi, plants, or animals, including active fragments and/or variants thereof.

The present disclosure relates to a pharmaceutical composition comprising an antibody or antibody fragment, a bispecific antibody, or an antibody conjugate according to the present disclosure, and optionally a pharmaceutically acceptable vector, a surfactant, and/or a diluent. In some embodiments, the pharmaceutical composition further comprises one or more additional therapeutic agents, in addition to the antibody, the bispecific antibody or the antibody conjugate according to the present disclosure. In some embodiments, the additional therapeutic agents include, but are not limited to, chemotherapeutic agents, growth inhibitors, cytotoxic agents, reagents for radiotherapy, anti-angiogenic agents, apoptotic agents, anti-tubulin agents, and others reagents for the treatment of cancer.

The term "multi-specific antibody" refers to a bispecific, trispecific, or tetraspecific antibody. A multi-specific antibody is composed of fragments of two or more different antibodies and is therefore capable of binding to two, three, or four different antigens.

The bispecific antibodies according to the present disclosure may be extracted and purified from host cells using standard experimental methods. For example, a bispecific antibody containing an antibody Fc portion may be purified using protein A or protein G affinity chromatography. The purification method includes, but is not limited to, affinity chromatography, an ion exchange method, size exclusion chromatography, and a protein ultrafiltration method. The method for isolation and purification of a bispecific antibody according to the present disclosure also includes a combination of the above methods. "Purification" as used herein refers to the isolation and/or recovery of target components from cells, cell cultures or other natural components. The antibodies according to the present disclosure are all purified antibodies, unless otherwise specified. The term "isolated antibody" as used refers to an antibody that is substantially free of other molecules having different structures or antigenic specificities, and a bispecific antibody molecule is an isolated antibody that is substantially free of other antibody molecules.

The term "host cell" refers to a cell and its progeny into which an exogenous nucleic acid is introduced, which can be transformed or transfected with a nucleotide encoding a polypeptide, to thereby express the exogenous polypeptide. The host cells described in the present disclosure include, but are not limited to, CHO cells (Chinese hamster ovary cells), HEK293 cells (Human embryonic kidney cells 293), BHK cells (Baby Hamster Kidney cells), myeloma cells, yeast, insect cells, or prokaryotic cells such as *Escherichia coli*. It should be noted that the "host cell" described in the present disclosure not only refers to a cell into which an exogenous nucleic acid is introduced, but also includes a progeny of the cell. The progeny cells may undergo mutations during cell division, but they still fall within the scope of the term as described in the present disclosure.

The present disclosure further encompasses nucleic acid sequences encoding these polypeptide chains. In the process of expressing antibodies, nucleic acid sequences are inserted into suitable vectors, the vectors including but not limited to: plasmids, phage expression vectors, cosmids, artificial chromosomes, phages, and animal viruses. The expression vectors contain elements for regulating expression, including, but not limited to, promoters, transcription initiation sequences, enhancers, signal peptide sequences, etc. The promoters include, but are not limited to, T7 promoter, T3 promoter, SP6 promoter, β-actin promoter, EF-1α promoter, CMV promoter, and SV40 promoter. The expression vectors may be transferred into host cells using appropriate methods known in the art, including but not limited to: a calcium phosphate precipitation method, a liposome transfection method, an electroporation method, and a PEI (polyethylene imine) transfection method.

Example 1: Construction of Expression Vector

(1) Sequence Design of CD20×CD3 BsAb

The bispecific antibody in an implementation of the present disclosure includes three or four polypeptide chains (FIG. 1), respectively named the first heavy chain (comprising a variable region having an amino acid sequence as set forth in SEQ ID No: 2), the first light chain (comprising a variable region having an amino acid sequence as set forth in SEQ ID No: 4), the second heavy chain (comprising a variable region having an amino acid sequence as set forth in SEQ ID No: 6), the second light chain (comprising a variable region having an amino acid sequence as set forth in SEQ ID No: 10), or a scFv-Fc chain (having an amino acid sequence as set forth in SEQ ID No: 11, SEQ ID No: 12, SEQ ID No: 13, or SEQ ID No: 14; or comprising a variable region having an amino acid sequence as set forth in SEQ ID No: 2, SEQ ID No: 4, SEQ ID No: 6, SEQ ID No: 8, or SEQ ID No: 10), thereby forming an immunoglobulin domain that specifically binds to CD20, and a separate immunoglobulin domain that specifically binds to CD3, and a heterodimeric Fc region. The interaction of the two heavy chains or the interaction of one heavy chain with the scFv-Fc chain constitutes the form of a heterodimer, thereby forming the above-mentioned heterodimeric Fc region.

The variable region of the bispecific antibody that specifically bound to the extracellular region of human CD20 was composed of VH1 and VL1 (FIG. 1), and had a sequence derived from Ofatumumab which was a fully humanized monoclonal antibody (Patent No.: US2014093454A1).

The variable region of the bispecific antibody that specifically bound to human CD3 was composed of VH2 and VL2 (FIG. 1) and derived from a humanized sequence of a murine monoclonal antibody disclosed in Patent No.: CN201810263832.0.

The deamination of a CDR region affected the stability of an antibody and the ratio between acidic and basic peaks. In the present disclosure, CDR3 of VH2 contained a potential deamination site (VH2-CDR3 had an original sequence of HGNFG$\underline{N}$SYVSWFA). In certain embodiments, potential deamination was eliminated by an amino acid mutation. The CD20×CD3 BsAb with VH2-CDR3 containing no deamination mutation (VH2-CDR3 had a sequence of HGNFGN-TYVSWFA) was named V1, and the CD20×CD3 BsAb with VH2-CDR3 containing a N106T mutation (VH2-CDR3 had a sequence of amino acids 101-113 of SEQ ID NO: 8) was named V2. After expression and purification (Example 2 and Example 3), the binding ability of mutants V1 and V2 to CD3 antigen (Example 4) was verified and tumor killing tests were performed (Example 5).

Partial sequence of the Fc moiety of the antibody was modified according to a method described in PCT Patent WO2017034770A1 published by a publisher. The Fc moiety of one of the heavy chains had the following mutations: P395K, P396K, and V397K, and the mutant was labeled OA (SEQ ID No: 1); and the Fc moiety of the other heavy chain had the following mutations: T394D, P395D, and P396D, and the mutant was labeled OB (SEQ ID No: 7), so that a heavy-chain heterodimer was formed.

(2) Molecular Cloning of Expression Plasmid

The nucleic acid sequence of the first heavy chain and the nucleic acid sequence of the first light chain were artificially synthesized by using a universal molecular cloning method (Sambrook J F, E. F. et al., Molecular cloning: a laboratory manual. 4th ed. Cold Spring Harbor Laboratory Press, Cold Spring Harbor, New York: 2012). The first light chain of the antibody was cloned into a modified plasmid pCDNA3.1(+) (Invitrogen, catalog No. V790-20). The plasmid was modified by adding a human Interleukin-2 (IL-2) signal peptide sequence at the N-terminus of the multiple cloning site so that it can express and secrete antibodies in HEK293 cells. The resulting expression plasmid was labeled pCDNA3.1-CD20-LC. The first heavy chain was cloned into a plasmid pFUSE-hIgG1-Fc2 (InvivoGene), and the resulting expression plasmid was labeled pFUSE-CD20-HC-OB.

The nucleic acid sequence of the second heavy chain and the nucleic acid sequence of the second light chain were artificially synthesized by using a universal molecular cloning method. The second light chain was cloned into a modified plasmid pCDNA3.1(+) (Invitrogen, catalog No. V790-20). The plasmid was modified by adding a human Interleukin-2 (IL-2) signal peptide sequence at the N-terminus of the multiple cloning site so that it can express and secrete antibodies in HEK293 cells. The resulting expression plasmid was labeled pCDNA3.1-CD3-LC. The second heavy chain was cloned into a plasmid pFUSE-hIgG1-Fc2 (InvivoGene), and the resulting expression plasmids were labeled pFUSE-CD3-HC-OA and pFUSE-CD3-HC-OA-N106T (with VH2-CDR3 containing a N106T mutation).

Example 2: Transient Transfection and Expression of Bispecific Antibodies

An Endo-Free-Plasmid Maxi Kit (100) (purchased from OMEGA, product catalog No. D6926-04) was used for large-scale plasmid extraction, and the operation steps were carried out according to instructions provided in the kit.

HEK293 cells were cultured to a cell density of $2.0 \times 10^6$ to $3.0 \times 10^6$ cells/mL. The cell suspension was centrifuged for 5 min at a rotational speed of 1,000 rpm. The old culture supernatant was discarded, and the cells were resuspended using a fresh medium (OPM-291 CD05 Medium, purchased from Shanghai OPM Biosciences Co., Ltd.) to a density of $1.0 \times 10^6$ cells/mL. Co-transfection was performed according to the plasmid combinations provided in Table 1. The transfected cell suspensions were placed in culture shakers with 5% C02 at 37° C. at 120 rpm for 5 to 7 days for culture in the dark, and supplements were added on the fourth day.

TABLE 1

| Transient Transfection of CD20 × CD3 BsAb | | |
|---|---|---|
| Version of CD20 × CD3 BsAb | Expression Plasmid Combination for Transfection | Reference Sequences |
| V1 | pFUSE-CD20-HC-OB | SEQ ID NO: 1 (Amino acid sequence of the first heavy chain binding to CD20) |
| | pCDNA3.1-CD20-LC | SEQ ID NO: 3 (Amino acid sequence of the first light chain binding to CD20) |
| | pFUSE-CD3-HC-OA | SEQ ID NO: 5 (Amino acid sequence of the second heavy chain binding to CD3) |
| | pCDNA3.1-CD3-LC | SEQ ID NO: 9 (Amino acid sequence of the second light chain binding to CD3) |
| V2 | pFUSE-CD20-HC-OB | SEQ ID NO: 1 (Amino acid sequence of the first heavy chain binding to CD20) |
| | pCDNA3.1-CD20-LC | SEQ ID NO: 3 (Amino acid sequence of the first light chain binding to CD20) |
| | pFUSE-CD3-HC-OA-N106T | SEQ ID NO: 7 (Amino acid sequence of the second heavy chain binding to CD3) |
| | pCDNA3.1-CD3-LC | SEQ ID NO: 9 (Amino acid sequence of the second light chain binding to CD3) |

Example 3: Purification of Bispecific Antibodies

Figure 2:
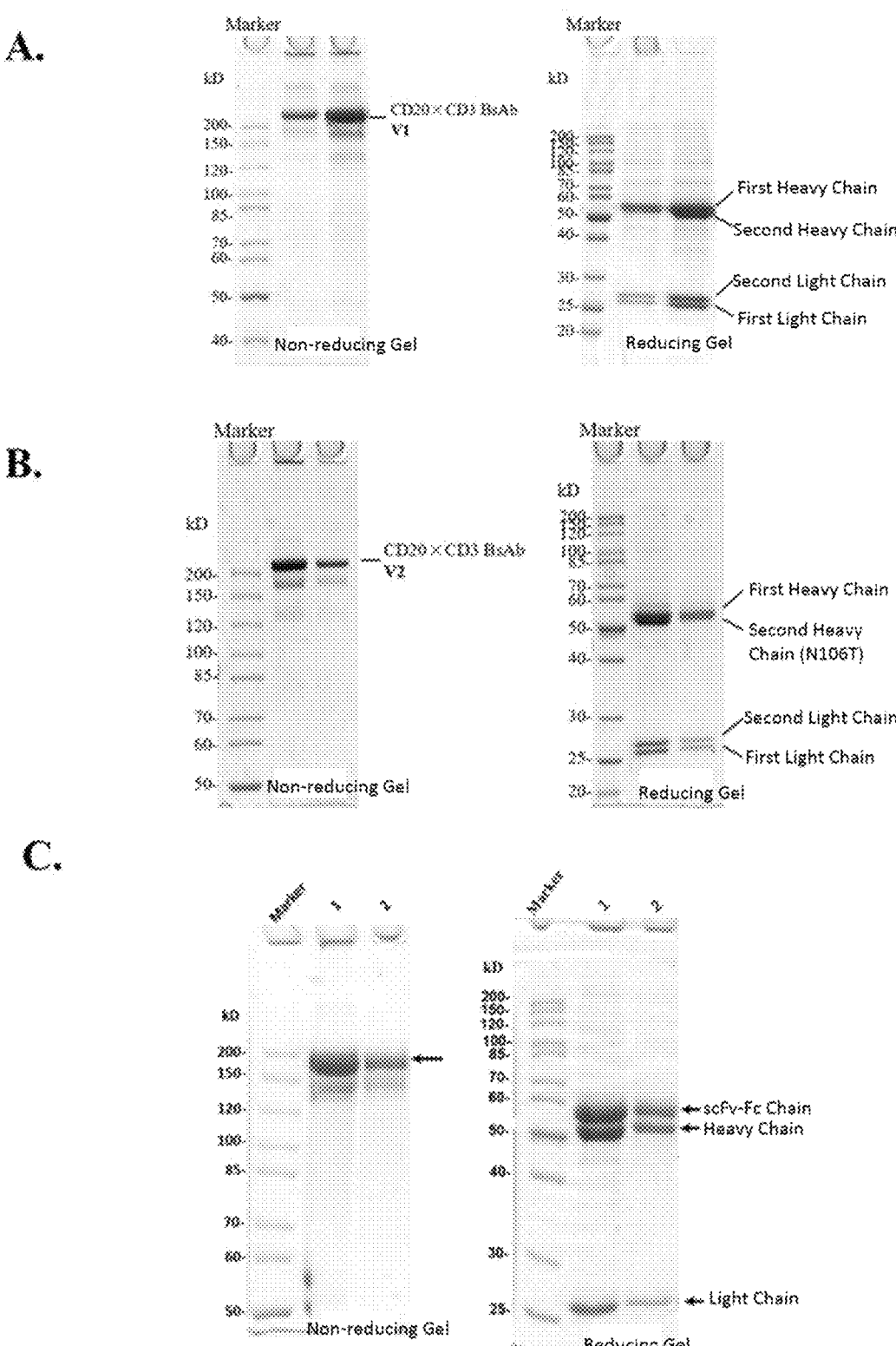

Each expression supernatant was collected by centrifugation. The cell supernatant was filtered with a 0.22 μm filter membrane. BsAb proteins were captured from the supernatant with an equilibrated protein A affinity chromatography filler (MabSelect SuRe™, purchased from GE Healthcare company, catalog No. 17-5438-02). Non-specifically bound proteins (about 10 column volumes) were removed with an equilibration buffer (137 mM NaCl, 2.7 mM KCl, 10 mM $Na_2HPO_4$, 1.8 mM $KH_2PO_4$), and then 5 to 10 column volumes were eluted with an elution buffer (100 mM glycine, pH 3.0 to pH 3.5). The eluate was collected and adjusted to a neutral pH with a neutralization buffer (1 M Tris-HCl, pH 9.0). The eluted proteins were analyzed by SDS-PAGE. FIGS. 2-A and 2-B showed that both V1 and V2 could reach high purity after the four-chain bispecific antibodies were purified with protein A in one step, and reducing electrophoresis showed that the ratio of the two heavy chains and the two light chains was approximate to 1:1:1:1. FIG. 2-C showed that the three-chain bispecific antibody had very high purity after purified with protein A in one step, and reducing electrophoresis showed that the ratio of the heavy chain, the light chain, and the scFv-Fc chain was approximate to 1:1:1.

Figure 3:
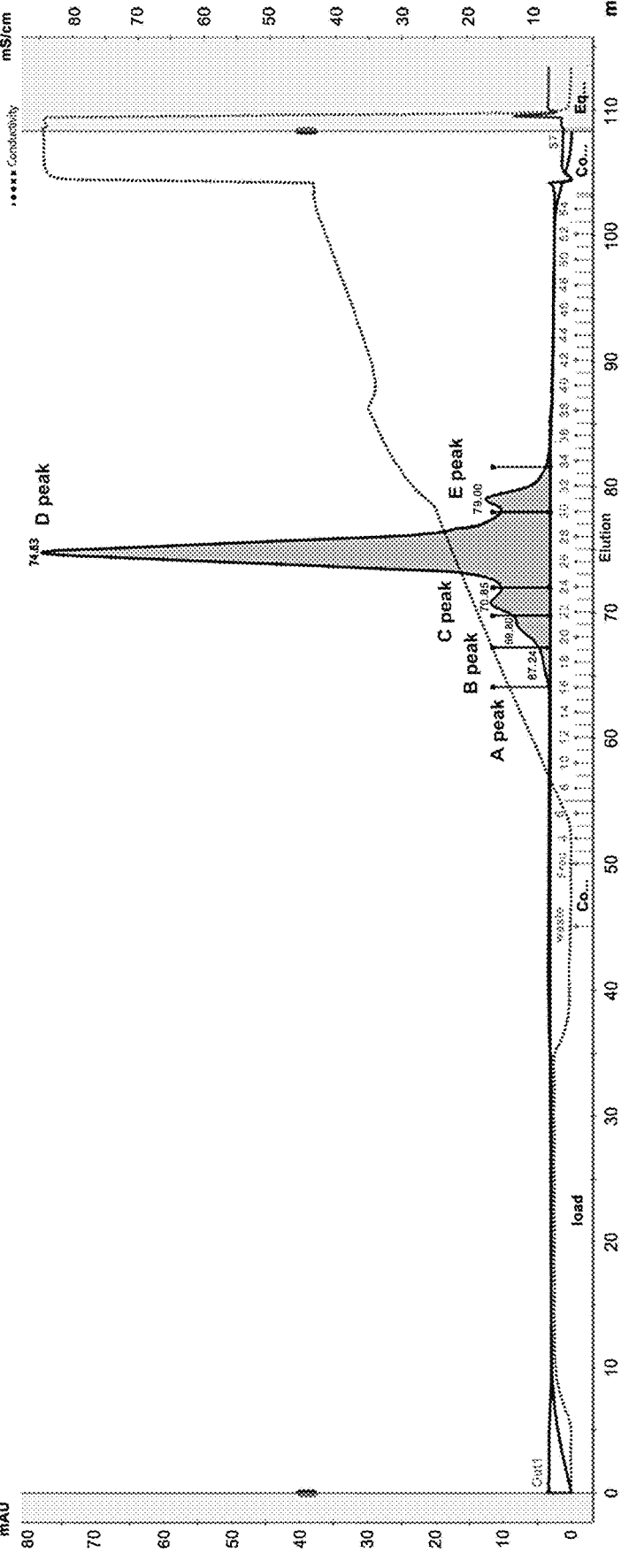
FIG. 3 is a graph showing A280 UV absorption peaks of CD20×CD3 BsAb V1 purified by a cation exchange chromatography (CEX) method, wherein a sample purified with protein A (FIG. 2A) is loaded onto a cation exchange column and eluted in a gradient with NaCl, and the eluted protein is collected by detecting the absorbance of ultraviolet light at 280 nm. One primary elution peak (peak D) and four small secondary elution peaks are formed by CD20×CD3 BsAb V1 through CEX.

Next, the proteins obtained after being eluted with protein A were further purified by using a AKTA pure 25 L1 protein purification system, and the eluted sample was loaded onto a equilibrated cation exchange column (prepacked column Resource™ S, 1 mL, GE Healthcare, product catalog No. 17-1178-01). Non-specifically bound proteins were removed with an equilibration buffer A (50 mM sodium phosphate, pH 6.0) until the UV absorption line was gentle. 15 column volumes were eluted linearly from 0% to 50% with an elution buffer B (50 mM sodium phosphate, 1 M NaCl, pH 6.0), and elution peaks were collected. FIG. 3 showed an elution curve.

Figure 4:
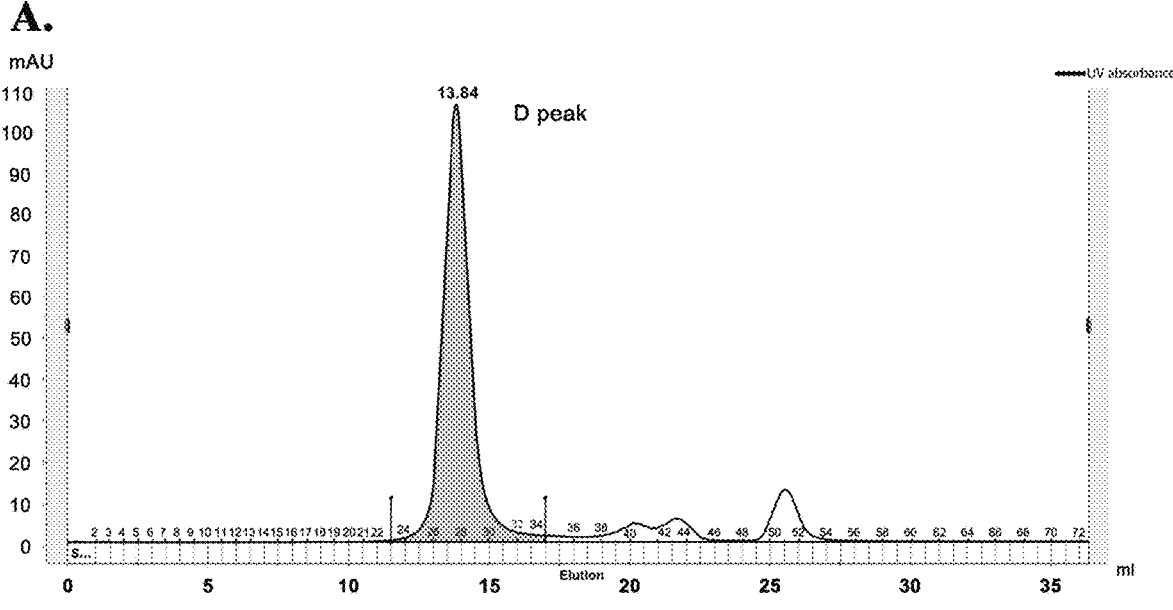
FIG. 4 shows elution curves of purification of bispecific antibodies, wherein FIG. (A) is a diagram showing an A280 UV absorption peak obtained by taking 1 mL of a sample purified with protein A (FIG. 2A) at a concentration of 1 mg/mL and analyzing the amount of aggregates in the sample purified with protein in one step by gel filtration chromatography (SEC); and figure (B) is a diagram showing an A280 UV absorption peak obtained by taking 1 mL of a sample purified with protein A (FIG. 2C, lane 1) at a concentration of 1 mg/mL and analyzing the amount of aggregates in the sample purified with protein in one step by gel filtration chromatography (SEC)
Figure 4:
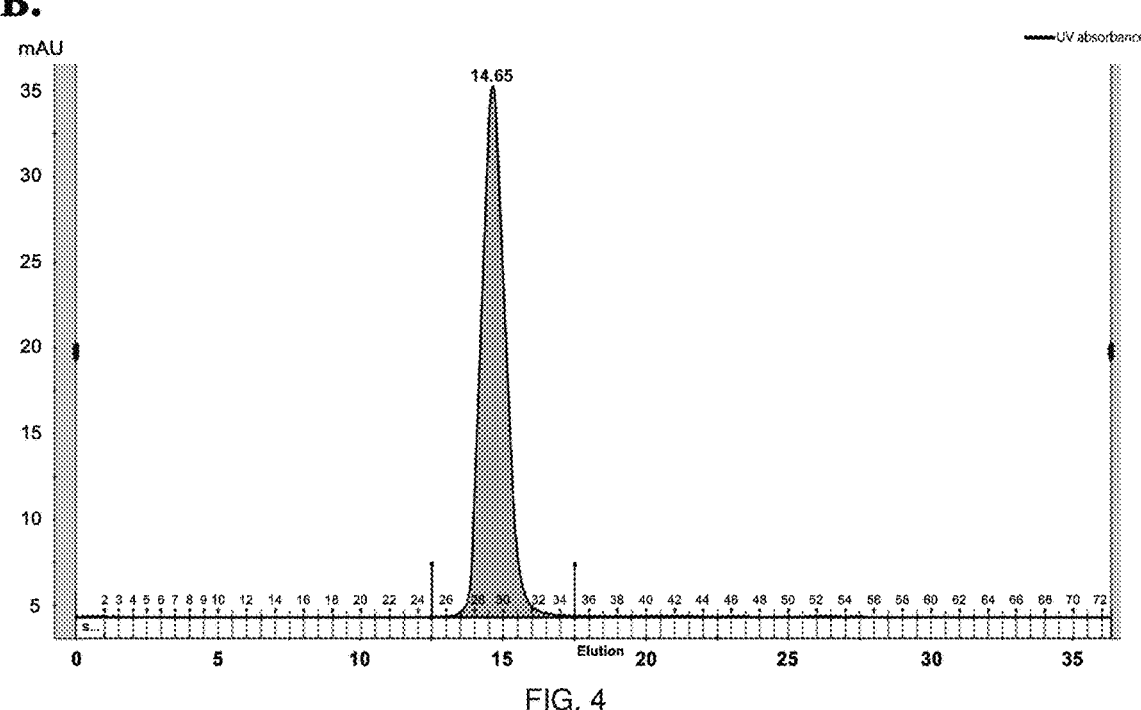

1 mL of the sample purified with protein A (at a concentration of 1 mg/mL) was taken, and the sample was loaded onto an equilibrated molecular sieve prepacked column (Superdex200 10/300GL increase, GE Healthcare, catalog No. 28-9909-44) by the 1 mL loading loop of the AKTA pure 25 L1 protein purification system. 1.5 column volumes were eluted with an equilibrate buffer (1×PBS buffer: 137 mM NaCl, 2.7 mM KCl, 10 mM $Na_2HPO_4$, 1.8 mM $KH_2PO_4$), and elution peaks were collected. FIG. 4 showed elution curves. SEC analysis showed that the CD20×CD3 BsAb V1 sample purified in one step (with protein A) had very few aggregates and contained more than 99% of monomers.

Example 4: Antibody Binding Activity Detection (ELISA)

(1) Detection of Binding Ability of CD20×CD3 Bispecific Antibodies to Antigen CD3 by ELISA In order to verify the binding ability of CD20×CD3 BsAbs to antigens, binding of the purified bispecific antibodies to antigen CD3 was detected by ELISA, respectively. The specific steps were carried out as follows.

1) The CD3 antigen used in this experiment was a 1:1 mixture of human CD3 e protein and human CD3 d protein, purchased from Sino Biological Inc.

2) Antigen Coating: the antigen was diluted to 100 ng/mL with 0.1 M sodium bicarbonate buffer (pH 9.5). The diluted antigen was added to the ELISA plate, 200 μL per well, the reaction wells were sealed with a plate sealing film, and the plate was placed at 4° C. for 16 hours. The plate was washed 5 times with 0.05% PBST.

3) Blocking: a 3% M-PBS blocking solution was prepared with skimmed milk powder and PBS buffer. 300 μL of 3% M-PBS was added to each well, and the reaction wells were sealed with a plate sealing film and incubated at room temperature for 1 hour. The plate was washed 5 times with 0.05% PBST.

4) Addition of Samples: the bispecific antibody sample was diluted with PBS to 10 μg/ml and then subjected to a 4-fold gradient dilution at a total of eight concentrations. The diluted samples were added at 100 μL/well, and two replicate wells were used for each antibody concentration. The reaction wells were sealed with a plate sealing film and incubated at room temperature for 1.5 hours. The plate was washed 5 times with 0.05% PBST.

5) Addition of Secondary Antibody: HRP-labeled Goat Anti-Human IgG (H+L) (purchased from Proteintech company, product catalog No. SA00001-17) was diluted with PBS at a ratio of 1:2000 and added in a volume of 100 μL to each well. The reaction wells were sealed with a plate sealing film and incubated at room temperature for 1 hour. The plate was washed 5 times with 0.05% PBST.

6) Chromogenesis: 100 μL of a TMB chromogenic solution was added to each well, and the plate was incubated at room temperature in the dark for 5 to 10 min.

7) Stopping: 50 μL of a stop solution (1 M HCl) was added to each well to stop the chromogenic reaction. After 3 min, the OD value of the reaction solution in each well was read at 450 nM on a microplate reader.

8) Data Analysis: data was processed using the software GraphPad Prism 5, and then a curve with the log (sample concentration) as the abscissa and the OD450 value as the ordinate was generated, and EC50 data was obtained.

Figure 5:
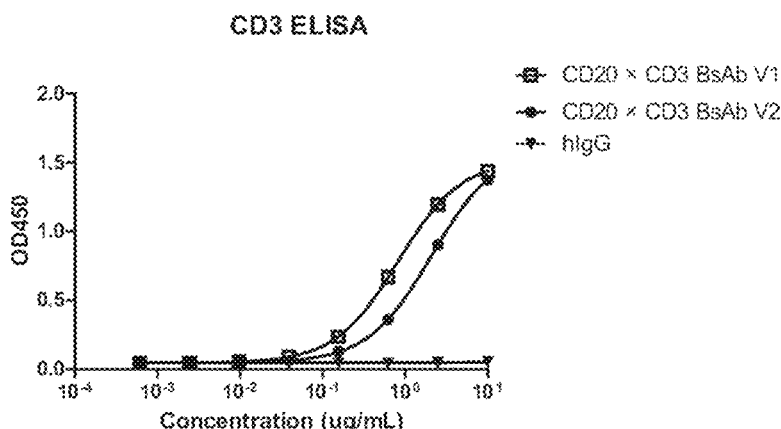
Figure 5:
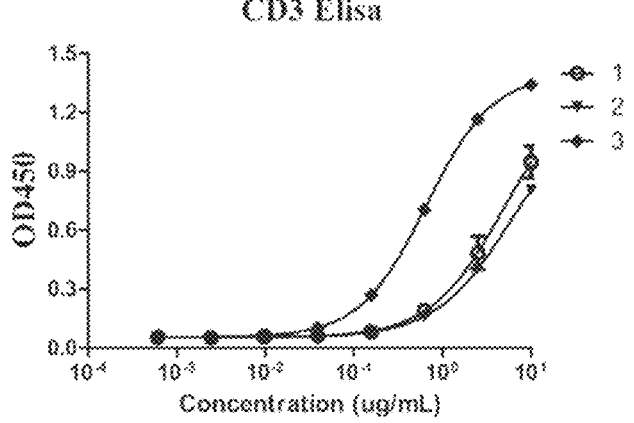

As shown in FIG. 5, the CD20×CD3 BsAb V1 bound to the CD3 antigen at an EC50 concentration of 0.8178 μg/mL, and the CD20×CD3 BsAb V2 bound to the CD3 antigen at an EC50 concentration of 2.097 μg/ml. V2 exhibited weak binding ability to the CD3 antigen, which indicated that the affinity of the antibody to CD3 was weakened by the introduction of N106T. In practical use, this characteristic will help avoid over-activation of T cells.

(2) Detection of Affinity of Bispecific Antibody Samples to CD20-Positive Cells by FACS In the present disclosure, Raji cells were used as cells positive for expression of CD20 and negative for expression of CD3 (i.e., CD20+/CD3−). The Raji cells were placed and cultured in an incubator with 5% C02 at 37° C., and the cells were collected when 80% to 90% of the cells were pooled. Meanwhile, the CD20×CD3 BsAb V1 and V2 samples were diluted to 20 μg/mL for subsequent use. The cells were washed twice with PBS buffer containing 1% FBS, and the cells were resuspended to $1×10^7$ cells/mL. 1.5 mL centrifuge tubes were taken, and 100 μL of the above cell suspension was added and 100 μL of the diluted sample was added to each tube. Each tube was mixed well and incubated on ice for 1 h. The tube was centrifuged (400 g, 5 min), the supernatant was discarded, and 1 mL of 1% FBS/PBS buffer was added to wash the cells twice. The cells were resuspended in PE-labeled goat anti-human IgG Fc (Invitrogen, Cat. 12-4998-82) and incubated on ice in the dark for 1 h. The tube was centrifuged again (400 g, 5 min), the supernatant was discarded, and 1 mL of 1% FBS/PBS buffer was added to wash the cells twice. Finally, the cells were resuspended in 200 μL of 1% FBS/PBS buffer, and the binding activity of the samples to Raji cells was detected by a flow cytometer.

The binding activity of the bispecific antibody samples to Raji cells was calculated and analyzed by the software Graphpad Prism 5.0, based on the average fluorescence intensity.

Figure 6:
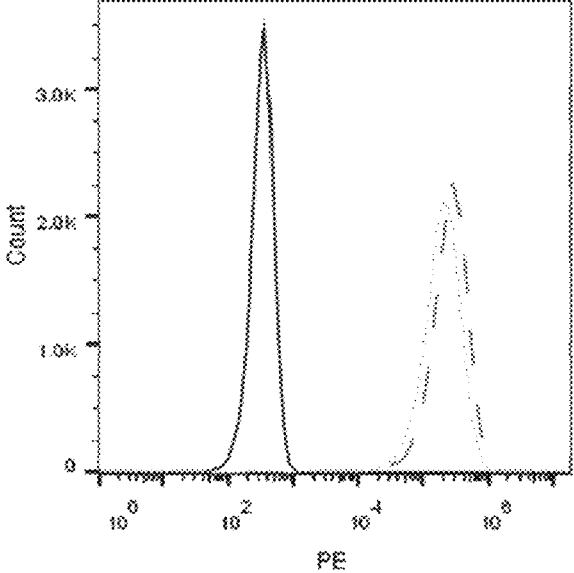
FIG. 6 is a graph showing the binding of CD20×CD3 BsAb V1 and CD20×CD3 BsAb V2 to cells positive for expression of CD20 (Raji cells) as detected by FACS.

As shown in FIG. 6, the CD20×CD3 BsAbs V1 and V2 exhibited the same binding activity to the CD20-positive Raji cells.

Example 5: Detection of In-Vitro Cytotoxicity Mediated by CD20×CD3 Bispecific Antibodies In order to further compare the tumor cell killing activity of the CD20×CD3 BsAbs V1 and V2 at the cellular level, ADCC toxicity detection of the purified bispecific antibody samples was performed in the present disclosure.

The specific steps were carried out as follows.

In the present disclosure, Raji cells were used as CD20-positive tumor cells. A Raji single cell suspension was prepared. The cell density was adjusted to $0.40×10^6$ cells/mL with a phenol red-free RPMI1640 medium containing 10% FBS. The cell suspension was added in a volume of 50 μL/well to a 96-well plate, thus there were $2.0×10^4$ cells per well. In this experiment, PBMCs were added in a quantity of 20 times more than the number of Raji cells, that is, $4.0×10^5$ cells/well, namely, 100 μL/well, thus the cell density was adjusted to $4.0×10^6$ cells/mL. The antibody was diluted to 0.1 μg/mL with a phenol red-free 10% FBS-RPMI 1640 medium, and then diluted at a ratio of 1:4 to obtain ten antibodies at concentrations of 100 ng/mL, 25 ng/mL, 6.25 ng/mL, 1.56 ng/mL, 0.39 ng/mL, 0.10 ng/mL, 0.02 ng/mL, and 0.006 ng/mL, respectively. According to the experimental design, corresponding antibodies were added in a volume of 50 μL/well, and the wells to which no antibody should be added were filled with the same volume of phenol red-free RPMI1640 medium containing 10% FBS. The cells were mixed uniformly with the antibodies and then cultured in an incubator with 5% $CO_2$ at 37° C. overnight. After about 20 hours elapsed, cellular cytotoxicity was detected using a lactate dehydrogenase cytotoxicity kit (purchased from Beyotime company), and then the killing activity of the CD20×CD3 BsAbs was detected by the following calculation formula:

$$\text{Killing Rate (\%)} = (OD_{sample} - S_{spontaneous}) / (Max - S_{spontaneous}) \times 100\% \text{ where } S_{spontaneous} = OD_{spontaneous \ release \ well \ (target \ cells + effector \ cells)}, Max = OD_{maximum \ release \ well \ (target \ cells)}.$$

Figure 7:
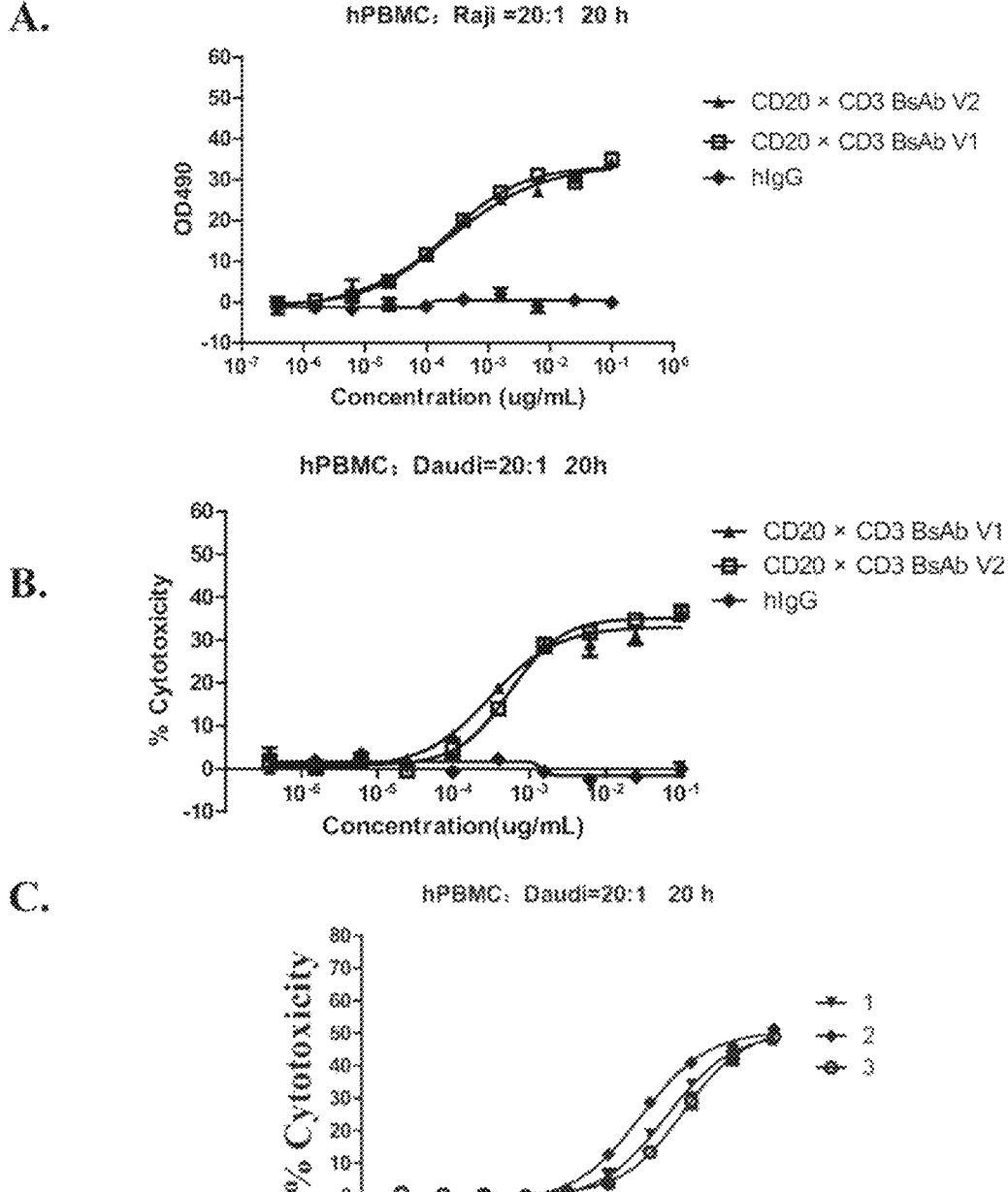
FIG. 7 shows ADCC cell killing experiments, wherein FIGS. 7A and B show the ADCC activity of CD20×CD3 BsAbs V1 and V2 to kill target tumor cells (Raji and Daudi cells), where V1 and V2 are significantly effective in killing tumor cells on which CD20 is highly expressed, both at an EC50 concentration of 0.2 ng/ml.
Figure 8:
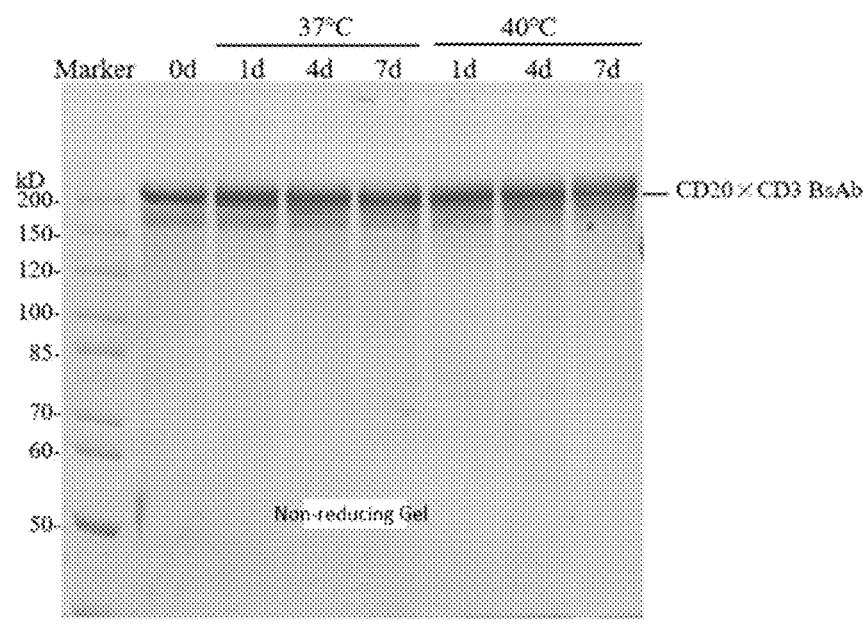
FIG. 8 shows a protein thermal stability test, showing diagrams of SDS-PAGE electrophoresis of protein samples which are placed at 37° C. and 40° C. for different time periods of 0 days, 1 day, 4 days, and 7 days.
Figure 8:
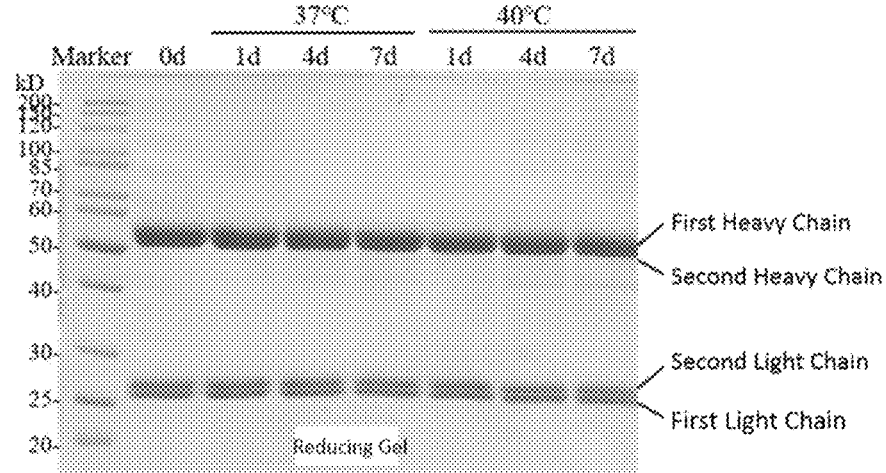

As shown in FIG. 7, the purified bispecific antibodies CD20×CD3 BsAbs V1 and V2 both can effectively mediate killing of CD20-positive tumor Raji cells by hPBMCs. Significant tumor cell killing effects were obtained, with EC50 concentrations of 0.21 ng/mL and 0.24 ng/ml, respectively. Although the CD20×CD3 BsAb V2 exhibited weaker affinity to CD3, its activity of killing target Raji cells was not affected.

Example 6: Antibody Stability Test

The CD20×CD3 BsAb V1 samples purified with protein A were respectively placed at 37° C. and 40° C. and placed for a period including: 0 d, 1 d, 4 d, and 7 d. The samples placed for different periods were analyzed by SDS-PAGE to detect the degradation situation and stability of the antibody at different temperatures. The results showed that the V1 samples could be stable at 37° C. and 40° C. for at least 7 days.

Example 7: Detection of Cytokine Release

PBMC cells were used in the present disclosure to measure the influence of bispecific antibodies on the release of cytokines. The PBMC cells were washed with PBS, and the cell density was adjusted so that each well contained $2 \times 10^5$ cells. Each antibody was diluted to 0.25 μg/mL with a 1640 medium, diluted in a gradient, and added to the above-mentioned wells. The 96-well plate was placed and cultured in an incubator with 5% C02 at 37° C. for 41 hours. The concentrations of cytokines in the samples were detected by a double antibody sandwich ELISA method. The specific method was carried out as follows: the above-mentioned 96-well plate containing PBMC cells was centrifuged at 1,000 rpm for 5 min, the supernatant was taken and added in a volume of 80 μL/well to the corresponding wells, and the reaction wells were sealed with a sealing film and incubated at room temperature for 120 minutes. The plate was washed 5 times, and then a biotinylated antibody was added in a volume of 100 μL/well, and the reaction wells were sealed with a sealing film and incubated at room temperature for 60 minutes. The plate was washed 5 times, and then HRP-streptavidin was added in a volume of 100 μL/well, and the reaction wells were sealed with a sealing film and incubated at room temperature in the dark for 10 to 20 minutes. The plate was washed 5 times, and then a TMB solution was added as a chromogenic agent in a volume of 100 μL/well, and the reaction wells were sealed with a sealing film and incubated at room temperature in the dark for 20 minutes. A stop solution was added in a volume of 50 μL/well. After the mixture was mixed well, the absorbance value at 450 nm was detected immediately using a microplate reader. The experimental results were shown in FIGS. 9A-9B.

Figure 9:
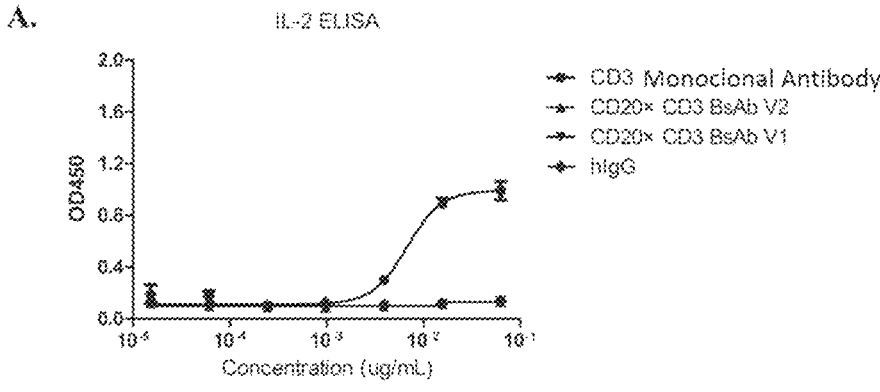
FIG. 9 is a graph showing a result of a test of cytokine release by a CD20×CD3 BsAb.
Figure 9:
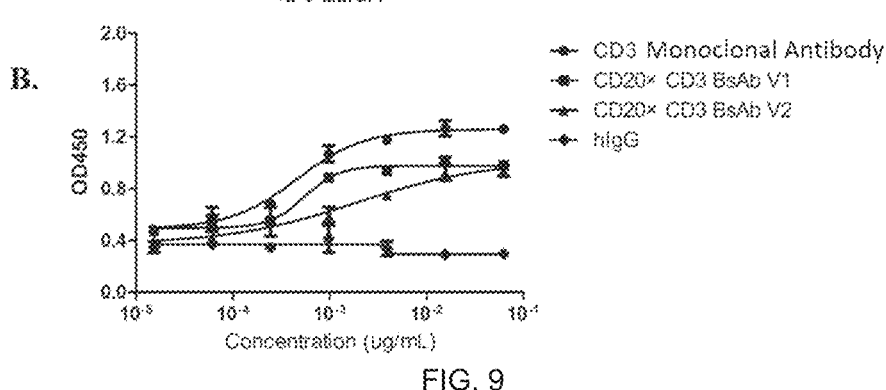

CD20×CD3 BsAb V1, CD20×CD3 BsAb V2, a CD3 monoclonal antibody, and IgG were incubated overnight together with PBMCs derived from different healthy donors, respectively, and the supernatants were taken and used in the above-mentioned ELISA sandwich experiment to detect the release of cytokines IL-2 and IL-6 so as to identify whether T cells are activated and produce cytokine release. The experimental data showed that, in the presence of target cells (B cells in PBMC), both bispecific antibodies CD20×CD3 BsAb V1 and CD20×CD3 BsAb V2 cannot induce IL-2 release (FIG. 9A), but can induced the release of IL-6 in an amount lower than that of the CD3 monoclonal antibody (FIG. 9B). V2 produces the lowest amount of IL-6. By the way, V2 contains a N106T mutation in its CD3 binding domain, which demonstrated lower affinity to CD3. This result indicated that the CD20×CD3 BsAbs in the present disclosure, especially V2, can only induce milder activation of T cells. If the CD20×CD3 bispecific antibodies of the present disclosure were used in clinical trial for treatment of CD20-positive B cell tumors, the occurrence of cytokine storms would be significantly reduced, and the safety profile of those antibodies will be improved dramatically.

Example 8: Detection of Anti-Tumor Activity in Mice

The in-vivo pharmacodynamic evaluation of CD20×CD3 BsAb was carried out based on a Raji subcutaneous xenograft tumor model positive for expression of CD20.

Figure 10:
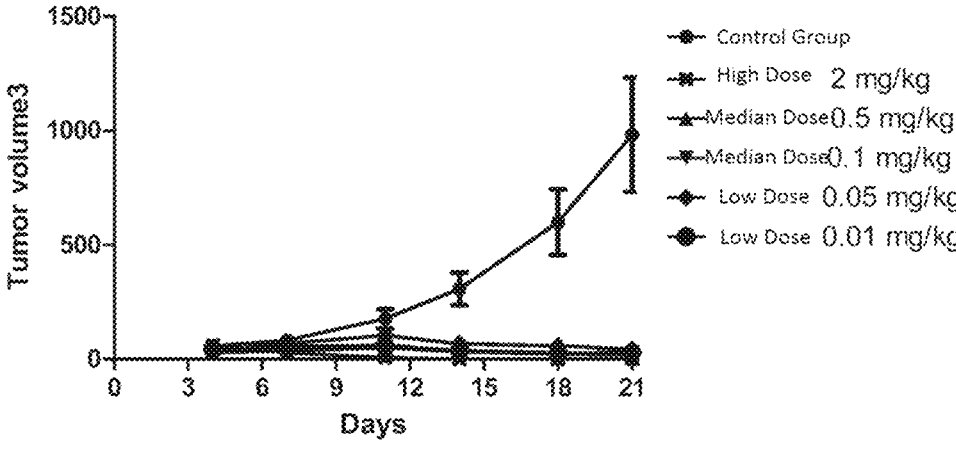
FIG. 10 is a graph showing the results of detection of anti-tumor activity in mice mediated by a CD20×CD3 BsAb.

Animal Model Establishment: Raji cells in a logarithmic growth phase were collected and mixed with PBMCs, and then inoculated subcutaneously on the back of NOD-SCID mice. The mice were randomly grouped into a control group and treatment groups. The bispecific antibody CD20×CD3 BsAb V1 of the present disclosure was administered according to the treatment groups at a low dose (0.01 mg/kg and 0.05 mg/mL), a median dose (0.1 mg/kg and 0.5 mg/mL), and a high dose (2 mg/kg) once on each of day 1, day 3, day 5, and day 8. An equal volume of sterile saline was administered to the negative control group. The long and short diameters of the tumors were measured and recorded once during grouping (i.e., before the first administration), twice a week after administration, and once before euthanasia to calculate the tumor volumes, and tumor growth curves were drawn according to the tumor volumes. The differences between the tumor growth curves of the respective groups were compared. The tumor volume was calculated according to the following formula: $V=1/2 \times \text{long diameter} \times (\text{short diameter})^2$. FIG. 10 showed the curves of tumor volumes as a function of time. The tumor volumes were measured twice a week, and changes in the weights of the mice were recorded. After the experiment was finished, the tumors were stripped and weighed.

As shown in FIG. 10, each of the groups treated with CD20×CD3 BsAb V1 (2 mg/kg, 0.5 mg/kg, 0.1 mg/kg, 0.05 mg/kg, 0.01 mg/kg) exhibited a significant tumor inhibiting effect after 21 days from the start of the treatment. All the treatment groups showed no animal deaths caused by treatment with the drug, no obvious drug toxicity and severe weight loss, and were well tolerated during the administration.

Finally, it should be noted that the above embodiments are merely intended to illustrate the technical solutions of the present disclosure, but not intended to limit the scope of the present disclosure. Although the present disclosure has been described in detail with reference to the preferred embodiments, it should be understood by those of ordinary skill in the art that the technical solutions of the present disclosure may be modified or equivalently replaced without departing from the spirit and scope of the technical solutions of the present disclosure.

INDUSTRIAL APPLICABILITY (1) Compared with monoclonal antibodies, CD20×CD3 BsAb molecules disclosed in the present application can simultaneously bind to antigens on the surface of tumor cells and to CD3 molecules on the surface of T cells, increase the targeted tumor killing effect of T cells by means of antigen-specific activation of TCR, therefore a significant tumor cell killing effect can be achieved with a smaller amount of antibodies.

(2) Compared with small molecular bispecific antibodies such as BiTE, the CD20×CD3 BsAb molecule according to the present disclosure contains an antibody Fc region, so that the half-life and stability of the antibody are increased, and it is easier to use the existing monoclonal antibody purification technology to simplify the production process of bispecific antibodies.

(3) Compared with CD20-targeting chimeric antigen receptor T-cell immunotherapy (CAR-T), the present disclosure does not involve exogenous viruses and operations such as in-vitro culture and reinfusion of T cells, and thus has fewer toxic and side effects and is safer and more controllable.

What is claimed is:

1. A bispecific antibody, comprising a domain capable of binding to CD20, a domain capable of binding to CD3 and a heterodimeric Fc region, wherein the domain capable of binding to CD20 is selected from the group consisting of a Fab region, a scFv region and a sDab region;

wherein the domain capable of binding to CD3 comprises a first immunoglobulin Fab region, wherein the first immunoglobulin Fab region is formed by a first heavy chain and a first light chain binding to each other, wherein a variable region of the heavy chain has the amino acid sequence as set forth in SEQ ID NO: 8, and a variable region of the light chain has the amino acid sequence as set forth in SEQ ID NO: 10;

and the heterodimeric Fc region is composed of two polypeptide chains, wherein each of the polypeptide chains contains opposite-charged amino acid modifications.

2. The bispecific antibody according to claim 1, wherein the domain capable of binding to CD20 comprises a second immunoglobulin Fab region, wherein the second immunoglobulin Fab region is formed by a second heavy chain and a second light chain binding to each other, and the second heavy chain and a CL portion of the second light chain both contain one non-cysteine residue substituted for a native cysteine residue and one cysteine residue substituted for a non-cysteine residue, wherein in the second heavy chain, the non-cysteine residue substituted for a native cysteine residue is C220S, and the cysteine residue substituted for a non-cysteine is L128C; and wherein in the CL portion of the second light chain, the non-cysteine residue substituted for a native cysteine residue is C214S, and the cysteine residue substituted for a non-cysteine is F118C.

3. The bispecific antibody according to claim 2, wherein the first immunoglobulin Fab region does not contain a non-cysteine residue substituted for a native cysteine residue and does not contain a cysteine residue substituted for a non-cysteine residue.

4. The bispecific antibody according to claim 1, wherein the domain capable of binding to CD20 comprises a second immunoglobulin Fab region and the second immunoglobu-lin Fab region is formed by a second heavy chain and a second light chain binding to each other; and the first heavy chain and the second heavy chain bind to each a other, to form a heterodimeric Fc region.

5. The bispecific antibody according to claim 4, wherein the first heavy chain and the second heavy chain comprise an Fc region selected from the group consisting of a human antibody IgG1, IgG2, IgG3 and IgG4.

6. The bispecific antibody according to claim 4, wherein the second heavy chain has the amino acid sequence as set forth in SEQ ID NO: 1, the second light chain has the amino acid sequence as set forth in SEQ ID NO: 3, the first heavy chain has the amino acid sequence as set forth in SEQ ID NO: 7, and the first light chain has the amino acid sequence as set forth in SEQ ID NO: 9.

7. The bispecific antibody according to claim 1, wherein the domain capable of binding to CD20 comprises a scFv-Fc fusion protein polypeptide chain, wherein the first heavy chain has the amino acid sequence as set forth in SEQ ID NO: 7, and the first light chain has the amino acid sequence as set forth in SEQ ID NO: 9, and the first immunoglobulin heavy chain and the scFv-Fc fusion protein a polypeptide chain bind to each other, to form a heterodimeric Fc region.

8. The bispecific antibody according to claim 7, wherein the first heavy chain has the amino acid as set forth in SEQ ID NO: 7, and a scFv region of the scFv-Fc fusion protein polypeptide chain has the amino acid as set forth in SEQ ID NO: 12, SEQ ID NO: 13 or SEQ ID NO: 14.

9. An antibody conjugate, wherein the antibody conjugate is formed by conjugating a substance to the bispecific antibody according to claim 7.

10. The antibody conjugate according to claim 9, wherein the substance is a cytotoxin, a radioisotope, a fluorescent label, a luminescent substance, a chromogenic substance or an enzyme.

11. A pharmaceutical composition, comprising the bispe-cific antibody according to claim 7.

12. A method for treating B cell lymphomas, rheumatoid arthritis, multiple sclerosis or systemic lupus erythematosus comprising administering to a subject in need thereof a therapeutically effective amount of the bispecific antibody according to claim 1.

* * * * *

SEQUENCE LISTING

<160> NUMBER OF SEQ ID NOS: 14

<210> SEQ ID NO 1
<211> LENGTH: 452
<212> TYPE: PRT
<213> ORGANISM: Artificial Sequence
<220> FEATURE:
<223> OTHER INFORMATION: pFUSE-CD20-HC-OB

<400> SEQUENCE: 1

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Cys Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Ser Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
```

-continued

```
            355                 360                 365
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Asp Asp
385                 390                 395                 400

Asp Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450

<210> SEQ ID NO 2
<211> LENGTH: 122
<212> TYPE: PRT
<213> ORGANISM: Artificial Sequence
<220> FEATURE:
<223> OTHER INFORMATION: a variable region of the first heavy chain;
      scFv-Fc fusion protein polypeptide chain

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Ala Met His Trp Val Arg Gln Ala Pro Gly Lys Gly Leu Glu Trp Val
            35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
                100                 105                 110

Gly Gln Gly Thr Thr Val Thr Val Ser Ser
        115                 120

<210> SEQ ID NO 3
<211> LENGTH: 214
<212> TYPE: PRT
<213> ORGANISM: Artificial Sequence
<220> FEATURE:
<223> OTHER INFORMATION: pCDNA3.1-CD20-LC

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

-continued

```
Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Cys Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Ser
    210
```

```
<210> SEQ ID NO 4
<211> LENGTH: 108
<212> TYPE: PRT
<213> ORGANISM: Artificial Sequence
<220> FEATURE:
<223> OTHER INFORMATION: a variable region of the first light chain;

<400> SEQUENCE: 4
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg
            100                 105
```

```
<210> SEQ ID NO 5
<211> LENGTH: 455
<212> TYPE: PRT
<213> ORGANISM: Artificial Sequence
<220> FEATURE:
<223> OTHER INFORMATION: pFUSE-CD3-HC-OA

<400> SEQUENCE: 5
```

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
```

-continued

```
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Lys Lys Lys Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455
```

<210> SEQ ID NO 6

```
<211> LENGTH: 125
<212> TYPE: PRT
<213> ORGANISM: Artificial Sequence
<220> FEATURE:
<223> OTHER INFORMATION: a variable region of the second heavy chain; a
      heavy chain variable region of a scFv region in the scFv-Fc fusion
      protein polypeptide chain

<400> SEQUENCE: 6

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 7
<211> LENGTH: 455
<212> TYPE: PRT
<213> ORGANISM: Artificial Sequence
<220> FEATURE:
<223> OTHER INFORMATION: pFUSE-CD3-HC-OA-N106T

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Met Tyr
                85                  90                  95

Tyr Cys Val Arg His Gly Asn Phe Gly Thr Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

-continued

```
Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
        260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Lys Lys Lys Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

```
<210> SEQ ID NO 8
<211> LENGTH: 125
<212> TYPE: PRT
<213> ORGANISM: Artificial Sequence
<220> FEATURE:
<223> OTHER INFORMATION: the variable region of the first heavy chain

<400> SEQUENCE: 8

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Met Tyr
                85                  90                  95
```

```
Tyr Cys Val Arg His Gly Asn Phe Gly Thr Ser Tyr Val Ser Trp Phe
            100             105             110

Ala Tyr Trp Gly Gln Gly Thr Leu Val Thr Val Ser Ser
        115             120             125

<210> SEQ ID NO 9
<211> LENGTH: 216
<212> TYPE: PRT
<213> ORGANISM: Artificial Sequence
<220> FEATURE:
<223> OTHER INFORMATION: pCDNA3.1-CD3-LC

<400> SEQUENCE: 9

Asp Ile Gln Met Thr Gln Glu Pro Ser Leu Thr Thr Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Ile Gly Gly Lys Ala Ala Leu Thr Ile Thr Gly Val
65                  70                  75                  80

Gln Pro Glu Asp Glu Ala Ile Tyr Phe Cys Ala Leu Trp Tyr Ser Asn
                85                  90                  95

Leu Trp Val Phe Gly Gly Gly Thr Lys Leu Glu Ile Lys Arg Thr Val
            100             105             110

Ala Ala Pro Ser Val Phe Ile Phe Pro Pro Ser Asp Glu Gln Leu Lys
        115             120             125

Ser Gly Thr Ala Ser Val Val Cys Leu Leu Asn Asn Phe Tyr Pro Arg
        130             135             140

Glu Ala Lys Val Gln Trp Lys Val Asp Asn Ala Leu Gln Ser Gly Asn
145             150             155             160

Ser Gln Glu Ser Val Thr Glu Gln Asp Ser Lys Asp Ser Thr Tyr Ser
                165             170             175

Leu Ser Ser Thr Leu Thr Leu Ser Lys Ala Asp Tyr Glu Lys His Lys
            180             185             190

Val Tyr Ala Cys Glu Val Thr His Gln Gly Leu Ser Ser Pro Val Thr
        195             200             205

Lys Ser Phe Asn Arg Gly Glu Cys
    210             215

<210> SEQ ID NO 10
<211> LENGTH: 110
<212> TYPE: PRT
<213> ORGANISM: Artificial Sequence
<220> FEATURE:
<223> OTHER INFORMATION: a variable region of the second light chain

<400> SEQUENCE: 10

Asp Ile Gln Met Thr Gln Glu Pro Ser Leu Thr Thr Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Pro Arg Gly
        35                  40                  45

Leu Ile Gly Gly Thr Asn Lys Arg Ala Pro Gly Thr Pro Ala Arg Phe
```

```
         50                55                60

Ser Gly Ser Leu Ile Gly Gly Lys Ala Ala Leu Thr Ile Thr Gly Val
65                70                75                80

Gln Pro Glu Asp Glu Ala Ile Tyr Phe Cys Ala Leu Trp Tyr Ser Asn
                  85                90                95

Leu Trp Val Phe Gly Gly Gly Thr Lys Leu Glu Ile Lys Arg
             100               105               110
```

<210> SEQ ID NO 11
<211> LENGTH: 250
<212> TYPE: PRT
<213> ORGANISM: Artificial Sequence
<220> FEATURE:
<223> OTHER INFORMATION: the scFv region in the scFv-Fc fusion protein
      polypeptide chain

<400> SEQUENCE: 11

```
Glu Val Gln Leu Val Glu Ser Gly Gly Gly Leu Val Gln Pro Gly Gly
1                 5                 10                15

Ser Leu Lys Leu Ser Cys Ala Ala Ser Gly Phe Thr Phe Asn Thr Tyr
             20                25                30

Ala Met Asn Trp Val Arg Gln Ala Pro Gly Lys Gly Leu Glu Trp Val
             35                40                45

Ala Arg Ile Arg Ser Lys Tyr Asn Asn Tyr Ala Thr Tyr Tyr Ala Asp
       50                55                60

Ser Val Lys Asp Arg Phe Thr Ile Ser Arg Asp Asp Ser Lys Asn Thr
65                70                75                80

Ala Tyr Leu Gln Met Asn Asn Leu Lys Thr Glu Asp Thr Ala Met Tyr
                  85                90                95

Tyr Cys Val Arg His Gly Asn Phe Gly Asn Ser Tyr Val Ser Trp Phe
             100               105               110

Ala Tyr Trp Gly Gln Gly Thr Leu Val Thr Val Ser Ser Gly Gly Gly
             115               120               125

Gly Ser Gly Gly Gly Gly Ser Gly Gly Gly Gly Ser Asp Ile Gln Met
       130               135               140

Thr Gln Glu Pro Ser Leu Thr Thr Ser Pro Gly Gly Thr Val Thr Leu
145               150               155               160

Thr Cys Arg Ser Ser Thr Gly Ala Val Thr Thr Ser Asn Tyr Ala Asn
             165               170               175

Trp Val Gln Glu Lys Pro Gly Gln Ala Pro Arg Gly Leu Ile Gly Gly
             180               185               190

Thr Asn Lys Arg Ala Pro Gly Thr Pro Ala Arg Phe Ser Gly Ser Leu
       195               200               205

Ile Gly Gly Lys Ala Ala Leu Thr Ile Thr Gly Val Gln Pro Glu Asp
       210               215               220

Glu Ala Ile Tyr Phe Cys Ala Leu Trp Tyr Ser Asn Leu Trp Val Phe
225               230               235               240

Gly Gly Gly Thr Lys Leu Glu Ile Lys Arg
             245               250
```

<210> SEQ ID NO 12
<211> LENGTH: 242
<212> TYPE: PRT
<213> ORGANISM: Artificial Sequence
<220> FEATURE:
<223> OTHER INFORMATION: the scFv region in the scFv-Fc fusion protein
      polypeptide chain

<400> SEQUENCE: 12

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Ser Tyr Leu Ala Trp Tyr Gln Gln Lys
                165                 170                 175

Pro Gly Gln Ala Pro Arg Leu Leu Ile Tyr Asp Ala Ser Asn Arg Ala
            180                 185                 190

Thr Gly Ile Pro Ala Arg Phe Ser Gly Ser Gly Ser Gly Thr Asp Phe
        195                 200                 205

Thr Leu Thr Ile Ser Ser Leu Glu Pro Glu Asp Phe Ala Val Tyr Tyr
    210                 215                 220

Cys Gln Gln Arg Ser Asn Trp Pro Ile Thr Phe Gly Gln Gly Thr Arg
225                 230                 235                 240

Leu Glu
```

<210> SEQ ID NO 13
<211> LENGTH: 248
<212> TYPE: PRT
<213> ORGANISM: Artificial Sequence
<220> FEATURE:
<223> OTHER INFORMATION: the scFv region in the scFv-Fc fusion protein
      polypeptide chain

<400> SEQUENCE: 13

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Gly Gly Gly Gly Ser Gly
```

-continued

```
                100              105              110
Gly Gly Gly Ser Gly Gly Gly Gly Ser Gly Gly Gly Gly Ser Glu Val
            115              120              125
Gln Leu Val Glu Ser Gly Gly Gly Leu Val Gln Pro Gly Arg Ser Leu
    130              135              140
Arg Leu Ser Cys Ala Ala Ser Gly Phe Thr Phe Asn Asp Tyr Ala Met
145              150              155              160
His Trp Val Arg Gln Ala Pro Gly Lys Gly Leu Glu Trp Val Ser Thr
                165              170              175
Ile Ser Trp Asn Ser Gly Ser Ile Gly Tyr Ala Asp Ser Val Lys Gly
                180              185              190
Arg Phe Thr Ile Ser Arg Asp Asn Ala Lys Lys Ser Leu Tyr Leu Gln
            195              200              205
Met Asn Ser Leu Arg Ala Glu Asp Thr Ala Leu Tyr Tyr Cys Ala Lys
    210              215              220
Asp Ile Gln Tyr Gly Asn Tyr Tyr Gly Met Asp Val Trp Gly Gln
225              230              235              240
Gly Thr Thr Val Thr Val Ser Ser
                245
```

```
<210> SEQ ID NO 14
<211> LENGTH: 247
<212> TYPE: PRT
<213> ORGANISM: Artificial Sequence
<220> FEATURE:
<223> OTHER INFORMATION: the scFv region in the scFv-Fc fusion protein
      polypeptide chain

<400> SEQUENCE: 14

Glu Ile Val Leu Thr Gln Ser Pro Ala Thr Leu Ser Leu Ser Pro Gly
1               5                10               15
Glu Arg Ala Thr Leu Ser Cys Arg Ala Ser Gln Ser Val Ser Ser Tyr
            20               25               30
Leu Ala Trp Tyr Gln Gln Lys Pro Gly Gln Ala Pro Arg Leu Leu Ile
            35               40               45
Tyr Asp Ala Ser Asn Arg Ala Thr Gly Ile Pro Ala Arg Phe Ser Gly
    50               55               60
Ser Gly Ser Gly Thr Asp Phe Thr Leu Thr Ile Ser Ser Leu Glu Pro
65               70               75               80
Glu Asp Phe Ala Val Tyr Tyr Cys Gln Gln Arg Ser Asn Trp Pro Ile
                85               90               95
Thr Phe Gly Gln Gly Thr Arg Leu Glu Gly Gly Gly Gly Ser Gly Gly
            100              105              110
Gly Gly Ser Gly Gly Gly Gly Ser Gly Gly Gly Gly Ser Glu Val Gln
            115              120              125
Leu Val Glu Ser Gly Gly Gly Leu Val Gln Pro Gly Arg Ser Leu Arg
    130              135              140
Leu Ser Cys Ala Ala Ser Gly Phe Thr Phe Asn Asp Tyr Ala Met His
145              150              155              160
Trp Val Arg Gln Ala Pro Gly Lys Gly Leu Glu Trp Val Ser Thr Ile
                165              170              175
Ser Trp Asn Ser Gly Ser Ile Gly Tyr Ala Asp Ser Val Lys Gly Arg
                180              185              190
Phe Thr Ile Ser Arg Asp Asn Ala Lys Lys Ser Leu Tyr Leu Gln Met
            195              200              205
```

-continued

```
Asn Ser Leu Arg Ala Glu Asp Thr Ala Leu Tyr Tyr Cys Ala Lys Asp
    210             215             220

Ile Gln Tyr Gly Asn Tyr Tyr Tyr Gly Met Asp Val Trp Gly Gln Gly
225             230             235             240

Thr Thr Val Thr Val Ser Ser
                245
```